United States Patent
Knook et al.

(10) Patent No.: US 11,224,360 B2
(45) Date of Patent: Jan. 18, 2022

(54) SYSTEMS AND METHODS FOR EVALUATING HEARING HEALTH

(71) Applicant: Mimi Hearing Technologies GmbH, Berlin (DE)

(72) Inventors: Guido Knook, Berlin (DE); Nicholas R. Clark, Royston (GB)

(73) Assignee: Mimi Hearing Technologies GmbH, Berlin (DE)

( * ) Notice: Subject to any disclaimer, the term of this patent is extended or adjusted under 35 U.S.C. 154(b) by 358 days.

(21) Appl. No.: 16/394,628

(22) Filed: Apr. 25, 2019

(65) Prior Publication Data
US 2020/0315498 A1 Oct. 8, 2020

(30) Foreign Application Priority Data
Apr. 2, 2019 (EP) .................................. 19166852

(51) Int. Cl.
*A61B 5/12* (2006.01)
*G16H 50/30* (2018.01)
*A61B 5/00* (2006.01)
*G10L 25/18* (2013.01)

(52) U.S. Cl.
CPC ............ *A61B 5/121* (2013.01); *A61B 5/7278* (2013.01); *G10L 25/18* (2013.01); *G16H 50/30* (2018.01)

(58) Field of Classification Search
CPC ....................... H04R 2225/39; H04R 2225/41; H04R 25/30; A61B 5/121; A61B 5/7278; A61B 5/7232; G16H 50/30; G10L 25/18; H04B 1/665
See application file for complete search history.

(56) References Cited

U.S. PATENT DOCUMENTS

2014/0294188 A1* 10/2014 Rini ....................... H04R 25/70
381/60

OTHER PUBLICATIONS

Hoth S, Baljić I. Current audiological diagnostics. GMS Curr Top Otorhinolaryngol Head Neck Surg. 2017;16:Doc09. Published Dec. 18, 2017. doi:10.3205/cto000148 (Year: 2017).*

* cited by examiner

*Primary Examiner* — Sean P Dougherty
*Assistant Examiner* — Alexander H Connor
(74) *Attorney, Agent, or Firm* — Polsinelli PC

(57) ABSTRACT

Systems and methods are provided for evaluating hearing health of a given user. An input audio signal is transformed into the frequency domain and a first and second hearing profile are applied to the input audio sample. The first hearing profile represents a healthy hearing standard and the second hearing profile is the given user's hearing profile. Using the hearing profiles, first and second perceptually relevant information (PRI) values are generated for the input audio sample. The first and second PRI values are analyzed against each other to generate a PRI index value for the given user, where the PRI index value is a hearing health index value for the given user. The given user's hearing profile may additionally be applied to differently processed audio samples to evaluate the amount of perceptual rescue offered by various digital signal processing algorithms.

19 Claims, 18 Drawing Sheets

SYSTEMS AND METHODS FOR EVALUATING HEARING HEALTH

CROSS-REFERENCE TO RELATED APPLICATIONS

This application claims priority to European Application No. 19166852.4 filed Apr. 2, 2019 and entitled "SYSTEMS AND METHODS FOR EVALUATING HEARING HEALTH", the disclosure of which is herein incorporated by reference in its entirety.

FIELD OF INVENTION

This invention relates generally to the field of audio engineering, psychoacoustics and digital signal processing, and more specifically relates to evaluating hearing health, for example by quantifying perceptually relevant information from a processed audio sample using custom psychoacoustic information.

BACKGROUND

Perceptual coders work on the principle of exploiting perceptually relevant information ("PRI") to reduce the data rate of encoded audio material. Perceptually irrelevant information, e.g., information that would not be heard by an individual, is discarded in order to reduce the data rate while maintaining the listening quality of the encoded audio. These "lossy" perceptual audio encoders are based on a psychoacoustic model of an ideal listener, e.g., a "golden ears" standard of normal hearing. To this extent, audio files are intended to be encoded once and then decoded using a generic decoder to make them suitable for general consumption by all listeners. Indeed, this paradigm forms the basis of MP3 encoding and other similar encoding formats, which revolutionized music file sharing in the 1990s by significantly reducing audio file sizes, ultimately leading to the success of music streaming services today.

PRI estimation generally consists of transforming a sampled window of an audio signal into the frequency domain, for example by using a fast Fourier transform ("FFT"). Masking thresholds are then obtained using psychoacoustic rules: critical band analysis is performed, noise-like or tone-like regions of the audio signal are determined, thresholding rules for the signal are applied and absolute hearing thresholds are subsequently accounted for. For instance, as part of this masking threshold process, quieter sounds within a similar frequency range to loud sounds are disregarded (i.e., they fall into the quantization noise when there is bit reduction), as well as quieter sounds immediately following loud sounds within a similar frequency range. Additionally, sounds occurring below the absolute hearing threshold are removed. Following this, the number of bits required to quantize the spectrum without introducing perceptible quantization error is determined. The result is approximately a ten-fold reduction in file size.

As mentioned previously, this approach uses a "golden ears" standard, that is, a standard that uses the threshold and masking threshold values of a healthy auditory system. However, this standard fails to take into account the individual hearing capabilities of a listener. Indeed, there are clear, discernable trends of hearing loss with increasing age (see, e.g., FIG. 1A, depicting audiograms by age group and sex in which increasing hearing loss is apparent with advancing age). Although hearing loss typically begins at higher frequencies, listeners who are aware that they have hearing loss do not typically complain about the absence of high frequency sounds. Instead, they report difficulties listening in a noisy environment and in perceiving details in a complex mixture of sounds. In essence, for hearing impaired ("HI") individuals, intense sounds more readily mask auditory information with energy at other frequencies. For example, music that was once clear and rich in detail becomes muddled. As hearing deteriorates, the signal-conditioning capabilities of the ear begin to break down, and thus HI listeners need to expend more mental effort to make sense of sounds of interest in complex acoustic scenes (or miss the information entirely). A raised threshold in an audiogram is not merely a reduction in aural sensitivity, but a result of the malfunction of some deeper processes within the auditory system that have implications beyond the detection of faint sounds. It follows that the perceptually-relevant information rate in bits/second, i.e., PRI, which is perceived by a listener with impaired hearing, is reduced relative to that of a normal hearing person due to higher thresholds and greater masking from other components of an audio signal within a given time frame.

To this extent, PRI loss would be a useful measure to communicate hearing health information to an individual, as PRI loss consolidates both threshold and masking threshold information across the audible spectrum into one value. Additionally, PRI loss is more readily understandable for a user because it provides a basis for more tangible comparisons. For example, for a given song, a PRI loss percentage value may be outputted to a listener, displaying that the listener only hears 85% of the given song's audible content. Similarly, a listener can examine how much of recorded speech content they can perceive.

Moreover, PRI loss may be partially reversed through the use of digital signal processing (DSP) techniques that reduce masking within an audio signal, such as through the use of multiband compressive systems (commonly used in hearing aids). To this extent, using PRI values to assess parameterized DSP systems could additionally communicate the perceptual rescue effects of a given DSP algorithm to a listener. This would further enable the listener to cross-compare the efficacy of hearing aids and/or sound personalization DSPs.

SUMMARY OF THE INVENTION

It is an object of this invention to provide improved systems and methods for evaluating hearing health as well as evaluating the perceptual rescue effects of different DSP systems. The problems raised in the known prior art will be at least partially solved in the invention as described below. The features according to the invention are specified within the independent claims, advantageous implementations of which will be shown in the dependent claims. The features of the claims can be combined in any technically meaningful way, and the explanations from the following specification as well as features from the figures which show additional embodiments of the invention can be considered.

One aspect of the present disclosure is to employ PRI calculations based on custom psychoacoustic models to provide a more accurate evaluation of a listener's hearing health as well as to provide an improved method to compare the perceptual rescue effects offered by various DSP systems. By using a listener's threshold and suprathreshold information to calculate a PRI value from a processed audio sample, the present disclosure integrates complex psychoacoustic data to better convey hearing health information. To this extent, the present disclosure provides an improved method for evaluating hearing health, optionally in combination with improved means to compare the listening benefits of different DSPs and/or hearing aid algorithms.

According to an aspect of the present disclosure, a method for measuring the hearing health of a user (also referred to herein as a listener) includes transforming an audio sample into the frequency domain. A healthy-standard hearing profile and a user hearing profile are applied to the transformed audio sample to calculate the perceptually relevant information (PRI) of the audio signal for each hearing profile. The healthy-standard and user hearing profiles each bear masked threshold and hearing threshold data. The values generated from each hearing profile are then analyzed in order to generate an index value indicative of the user's hearing health.

In a further aspect of the present disclosure, an audio sample may be processed using a parameterized processing function. The user hearing profile may then be applied to the processed audio sample to generate a further PRI value indicative of the perceptual rescue effected by the parameterized DSP.

In another embodiment, more than one parameterized processing function may be used to process the audio sample to allow the user to compare the perceptual rescue effected by various DSP systems. The multiple DSP systems may be the same DSP algorithm that is differently parameterized, may be entirely different DSP algorithms, or may be any combination of the above.

In an embodiment of the present disclosure, the hearing profile is derived from at least one of a suprathreshold test, a psychophysical tuning curve (PTC), a masked threshold (MT) curve, a threshold test and an audiogram.

In an embodiment of the present disclosure, the user's hearing profile may be estimated from the user's demographic information, which may include age and sex information.

In an embodiment of the present disclosure, the parameters of the parameterized processing function may be optimized for their PRI value to convey to the user the maximal perceptual rescue effected by the processing function. Sub-optimal parameters may also be used to convey the perceptual rescue effects of under-processed or over-processed audio, by employing an iterative optimization approach using PRI as optimization criterion. The PRI based on a specific user's individual hearing profile is calculated for a processed audio signal and the processing parameters are adapted, e.g., based on the feedback PRI, so as to optimize the output PRI value for the specific user's individual hearing profile. This process may be repeated in an iterative way. Eventually, the audio signal is processed with the optimal parameters determined by this optimization approach and a final representation of the audio signal is thereby generated.

The determining of the optimized processing parameters may comprise a sequential determination of subsets of the processing parameters, each subset determined so as to optimize the user's PRI for the audio signal. In other words, only a subset of the processing parameters may be considered at the same given time during the optimization. Other parameters are then taken into account in further optimization steps. This reduces the dimensionality for the optimization procedure and allows faster optimization and/or usage of simpler optimization algorithms such as brute force search to determine the parameters. For example, the processing parameters can be determined sequentially on a subband by subband basis.

In an aspect of the present disclosure, the selection of a subset of the subbands for parameter optimization may be such that a masking interaction between the selected subbands is minimized. The optimization may then determine the processing parameters for the selected subbands. Since there is little to no masking interaction amongst the selected subbands of the subset, the optimization of processing parameters can be performed separately for the selected subbands. For example, subbands largely separated in frequency typically have little masking interaction with one another and can thus be optimized individually.

Methods of the present disclosure may further comprise determining at least one processing parameter for an unselected subband based on the processing parameters of adjacent subbands that have previously been determined. For example, the at least one processing parameter for an unselected subband can be determined based on an interpolation of the corresponding processing parameters of the adjacent subbands. Thus, it is not necessary to determine the parameters of all subbands by the optimization method, which may be computationally expensive and time consuming. Methods of the present disclosure can be used, for example, to perform parameter optimization for every other subband and to then interpolate the parameters of the missing subbands from the parameters of the adjacent subbands.

In an aspect of the present disclosure, the selection of subbands for parameter optimization may be performed as follows: first selecting a subset of adjacent subbands; tying the corresponding values of the at least one parameter for the selected subbands; and then performing a joint determination of the tied parameter values by minimizing the user's PRI for the selected subbands. For example, a number n of adjacent subbands is selected and the corresponding values of parameters of the selected subbands are tied. For example, only a single compression threshold and a single compression ratio might be considered for the subset, and the user's PRI for the selected subbands is minimized by searching for the best threshold and gain values.

Methods of the present disclosure may continue by selecting a reduced subset of adjacent subbands from the selected initial subset of subbands and tying the corresponding values of the at least one parameter for the reduced subset of subbands. For example, the subbands at the edges of the initial subset as determined above are dropped, resulting in a reduced subset with a smaller number n−2 of subbands. A joint determination of the tied parameters is performed by minimizing the user's PRI for the reduced subset of subbands. This will provide a new solution for the tied parameters of the reduced subset, e.g., a threshold and a ratio for the subbands of the reduced subset. The new parameter optimization for the reduced subset may be based on the results of the previous optimization for the initial subset. For example, when performing the parameter optimization for the reduced subset, the solution parameters from the previous optimization for the initial subset may be used as a starting point for the new optimization. The previous steps may be repeated, and the subsets subsequently reduced, until a single subband remains and is selected. The optimization may then continue with determining the at least one parameter of the single subband. Again, this last optimization step may be based on the previous optimization results, e.g., by using the previously determined parameters as a starting point for the final optimization. It is noted that the above processing steps can be applied on a parameter by parameter basis, i.e., operating separately on thresholds, ratios, gains, etc.

In embodiments of the present disclosure, the optimization method begins again with another subset of adjacent subbands and repeats the previous steps of determining the at least one parameter of a single subband by successively reducing the another selected initial subset of adjacent subbands. When only a single subband remains as a result of the continued reduction of subbands in the selected subsets, the parameters determined for the single subband derived from the initial subset and the single subband derived from the another initial subset are jointly processed to determine the parameters of the single subband derived from the initial subset and/or the parameters of the single subband derived from the another initial subset. The joint processing of the parameters for the derived single subbands may comprise at least one of: joint optimization of the parameters for the derived single subbands; smoothing of the parameters for the derived single subbands; and application of constraints on the deviation of corresponding values of the parameters for the derived single subbands. Thus, the parameters of the single subband derived from the initial subset and the parameters of the single subband derived from the another initial subset can be made to comply with given conditions such as limiting their distances or deviations to ensure a smooth contour or course of the parameters across the subbands. Again, the above processing steps can be applied on a parameter by parameter basis, i.e., operating separately on thresholds, ratios, gains, etc.

Unless otherwise defined, all technical terms used herein have the same meaning as commonly understood by one of ordinary skill in the art to which this technology belongs. The term "audio device", as used herein, is defined as any device that outputs audio, including, but not limited to: mobile phones, computers, televisions, hearing aids, headphones and/or speaker systems.

The term "hearing profile", as used herein, is defined as an individual's hearing data attained, by example, through: administration of a hearing test or tests, from a previously administered hearing test or tests attained from a server or from a user's device, or from an individual's sociodemographic information, such as from their age and sex, potentially in combination with personal test data. The hearing profile may be in the form of an audiogram and/or from a suprathreshold test, such as a psychophysical tuning curve test or masked threshold test.

The term "masking thresholds", as used herein, is the intensity of a sound required to make that sound audible in the presence of a masking sound. Masking may occur before onset of the masker (backward masking), but more significantly, occurs simultaneously (simultaneous masking) or following the occurrence of a masking signal (forward masking). Masking thresholds depend on the type of masker (e.g. tonal or noise), the kind of sound being masked (e.g. tonal or noise) and on the frequency. For example, noise more effectively masks a tone than a tone masks a noise. Additionally, masking is most effective within the same critical band, i.e. between two sounds close in frequency. Individuals with sensorineural hearing impairment typically display wider, more elevated masking thresholds relative to normal hearing individuals. To this extent, a wider frequency range of off frequency sounds will mask a given sound. Masking thresholds may be described as a function in the form of a masking contour curve. A masking contour is typically a function of the effectiveness of a masker in terms of intensity required to mask a signal, or probe tone, versus the frequency difference between the masker and the signal or probe tone. A masker contour is a representation of the user's cochlear spectral resolution for a given frequency, i.e. place along the cochlear partition. It can be determined by a behavioral test of cochlear tuning rather than a direct measure of cochlear activity using laser interferometry of cochlear motion. A masking contour may also be referred to as a psychophysical or psychoacoustic tuning curve (PTC). Such a curve may be derived from one of a number of types of tests: for example, it may be the results of Brian Moore's fast PTC, of Patterson's notched noise method or any similar PTC methodology, as would be appreciated by one of ordinary skill in the art. Other methods may be used to measure masking thresholds, such as through an inverted PTC paradigm, wherein a masking probe is fixed at a given frequency and a tone probe is swept through the audible frequency range (i.e. a masking threshold test).

The term "hearing thresholds", as used herein, is the minimum sound level of a pure tone that an individual can hear with no other sound present. This is also known as the "absolute threshold" of hearing. Individuals with sensorineural hearing impairment typically display elevated hearing thresholds relative to normal hearing individuals. Absolute thresholds are typically displayed in the form of an audiogram.

The term "masking threshold curve", as used herein, represents the combination of a user's masking contour and a user's absolute thresholds.

The term "perceptual relevant information" or "PRI", as used herein, is a general measure of the information rate that can be transferred to a receiver for a given piece of audio content after taking into consideration in what information will be inaudible due to having amplitudes below the hearing threshold of the listener, or due to masking from other components of the signal. The PRI information rate can be described in units of bits per second (bits/second).

The term "perceptual rescue", as used herein, is a general measure of the net increase in PRI that a digital signal processing algorithm offers for a given audio sample for a user. This is achieved by increasing the audibility of an audio signal. This results, for instance, in an increase in the units of bits per second (bits/second).

The term "multi-band compression system", as used herein, generally refers to any processing system that spectrally decomposes an incoming audio signal and processes each subband signal separately. Different multi-band compression configurations may be possible, including, but not limited to: those found in simple hearing aid algorithms, those that include feedforward and feedback compressors within each subband signal (see e.g. commonly owned European Patent Application 18178873.8), and/or those that feature parallel compression (wet/dry mixing).

The term "threshold parameter", as used herein, generally refers to the level, typically decibels Full Scale (dB FS) above which compression is applied in a DRC.

The term "ratio parameter", as used herein, generally refers to the gain (if the ratio is larger than 1) or attenuation (if the ratio is a fraction between zero and one) per decibel exceeding the compression threshold. In an embodiment of the present disclosure, the ratio comprises a fraction between zero and one.

The term "imperceptible audio data", as used herein, generally refers to any audio information an individual cannot perceive, such as audio content with amplitude below hearing and masking thresholds. Due to raised hearing thresholds and broader masking curves, individuals with sensorineural hearing impairment typically cannot perceive as much relevant audio information as a normal hearing individual within a complex audio signal. In this instance, perceptually relevant information is reduced.

The term "quantization", as used herein, refers to representing a waveform with discrete, finite values. Common quantization resolutions are 8-bit (256 levels), 16-bit (65,536 levels) and 24-bit (16.8 million levels). Higher quantization resolutions lead to less quantization error, at the expense of file size and/or data rate.

The term "frequency domain transformation", as used herein, refers to the transformation of an audio signal from the time domain to the frequency domain, in which component frequencies are spread across the frequency spectrum. For example, a Fourier transform converts the time domain signal into an integral of sine waves of different frequencies, each of which represents a different frequency component.

The phrase "computer readable storage medium", as used herein, is defined as a solid, non-transitory storage medium. It may also be a physical storage place in a server accessible by a user, e.g. to download for installation of the computer program on her device or for cloud computing.

One or more of the above aspects of the present disclosure, e.g. those aspects described with respect to methods of the present disclosure, may be similarly applied (without departing from the scope of the present disclosure) to an apparatus or system having at least one processor and at least one memory to store programming instructions or computer program code and data, the at least one memory and the computer program code configured to, with the at least one processor, cause the apparatus at least to perform the above functions. Alternatively, the above apparatus may be implemented by circuitry.

According to another aspect of the present disclosure, a computer program comprising instructions for causing an apparatus to perform any of the above methods is disclosed. Furthermore, a computer readable medium comprising program instructions for causing an apparatus to perform any of the above methods is disclosed.

Furthermore, a non-transitory computer readable medium is disclosed, comprising program instructions stored thereon for performing the above functions.

Implementations of the disclosed apparatus may include using, but is not limited to, one or more processors, one or more application specific integrated circuits (ASICs) and/or one or more field programmable gate arrays (FPGAs). Implementations of the apparatus may also include using other conventional and/or customized hardware such as software programmable processors.

It will be appreciated that method steps and apparatus features may be interchanged in many ways. In particular, the details of the disclosed apparatus can be implemented as a method, as will be appreciated by one of ordinary skill in the art.

Other and further embodiments of the present disclosure will become apparent during the course of the following discussion and by reference to the accompanying drawings.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof, which are illustrated in the appended drawings. Understand that these drawings depict only example embodiments of the disclosure and are not therefore to be considered to be limiting of its scope, the principles herein are described and explained with additional specificity and detail through the use of the accompanying drawings in which.

DETAILED DESCRIPTION

Figure 1A:
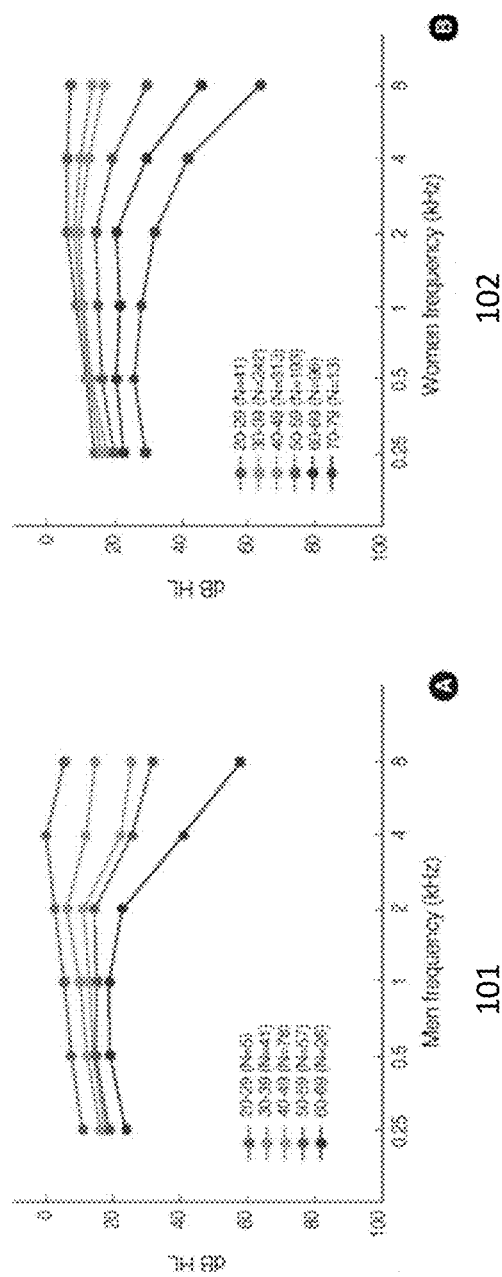
FIG. 1A illustrates representative audiograms by age group and sex in which increasing hearing loss is apparent with advancing age.

Various example embodiments of the present disclosure are discussed in detail below. While specific implementations are discussed, it is appreciated that these implementations are described for illustration purposes only. One of ordinary skill in the art will recognize that other components and configurations may be used without parting from the spirit and scope of the disclosure.

The present disclosure relates to creating improved systems and methods for evaluating hearing health as well as creating means to compare the perceptual rescue effects of different DSP systems using perceptually relevant information ("PRI") calculations. PRI is the information rate (bits/second) that can be transferred to a receiver for a given piece of audio content after factoring in what information will be lost because it is below the hearing threshold of the listener, or lost due to masking from other components of the signal within a given time frame. This is the result of a sequence of signal processing steps that are well defined for the ideal listener. In general terms, PRI is calculated from absolute thresholds of hearing (the minimum sound intensity at a particular frequency that a listener is able to detect) as well as the masking patterns for the particular listener.

Masking is a phenomenon that occurs across all sensory modalities where one stimulus component prevents detection of another. The effects of masking are present in the typical day-to-day hearing experience as individuals are rarely in a situation of complete silence with just a single pure tone occupying the sonic environment. To counter masking and allow the listener to perceive as much information within their surroundings as possible, the auditory system processes sound in way that provides a high bandwidth of information to the brain. The basilar membrane running along the center of the cochlea, which interfaces with the structures responsible for neural encoding of mechanical vibrations, is frequency selective. To this extent, the basilar membrane acts to spectrally decompose incoming sonic information whereby energy concentrated in different frequency regions is represented to the brain along different auditory fibers. The basilar membrane can be modelled as a filter bank with near logarithmic spacing of filter bands. This allows a listener to extract information from one frequency band, even if there is strong simultaneous energy occurring in a remote frequency region. For example, an individual will be able to hear both the low frequency rumble of a car approaching whilst listening to someone speak at a higher frequency. High energy maskers are required to mask signals when the masker and signal have different frequency content, but low intensity maskers can mask signals when their frequency content is similar.

The characteristics of auditory filters can be measured, for example, by playing a continuous tone at the center frequency of the filter of interest, and then measuring the masker intensity required to render the probe tone inaudible to a given listener as a function of relative frequency difference between masker and probe components. A psychophysical tuning curve (PTC), consisting of a frequency selectivity contour extracted via behavioral testing, provides useful data to determine a given individual's masking contours. In one embodiment of the test, a masking band of noise is gradually swept across frequency, from below the probe frequency to above the probe frequency. The given individual (i.e. the listener) then responds when he or she can hear the probe and stops responding when the probe can no longer be heard. This gives a jagged trace that can then be interpolated to estimate the underlying characteristics of the auditory filter of interest. It is appreciated that other methodologies known in the art may be employed to obtain user masking contour curves without departing from the scope of the present disclosure. For instance, an inverse paradigm may be used in which a probe tone is swept across frequency while a masking band of noise is fixed at a center frequency (known as a "masked threshold test" or "MT test").

Figure 1B:
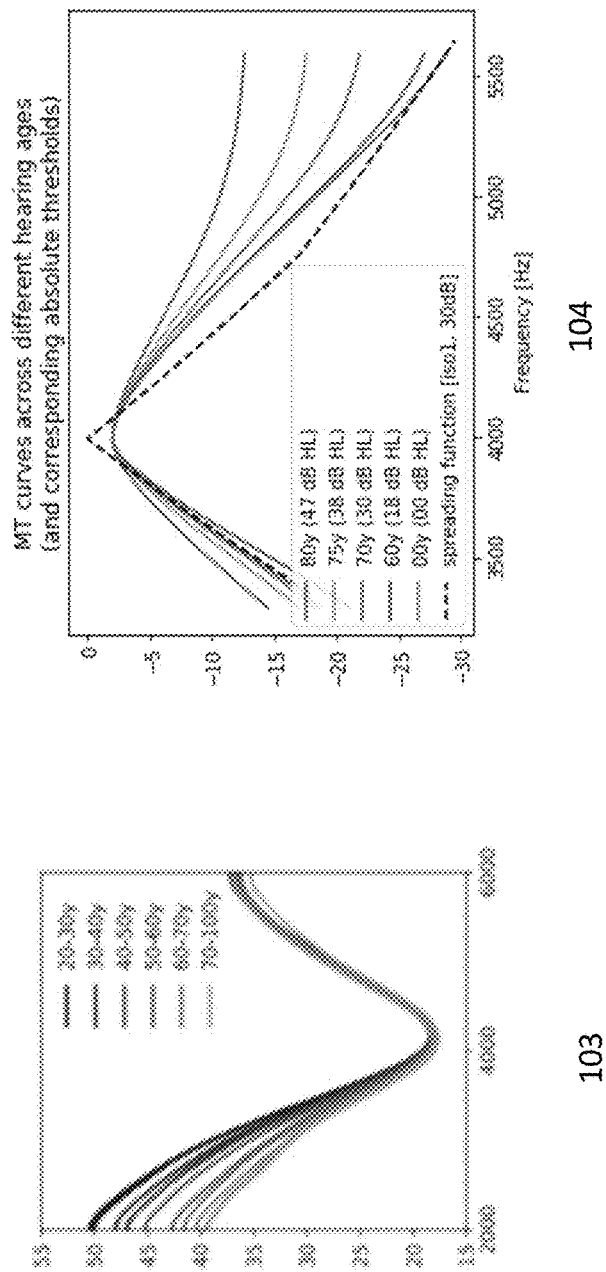
FIG. 1B illustrates a series of psychophysical tunings, which when averaged out by age, show a marked broadening of the masking contour curve.

Patterns begin to emerge when testing listeners with different hearing capabilities using the PTC test. For example, as seen in FIG. 1B, hearing impaired listeners have broader PTC curves 103 and MT curves 104, meaning maskers at remote frequencies are more effective. To this extent, each auditory nerve fiber of an HI (Hearing Impaired) listener contains information from neighboring frequency bands, resulting in increasing frequency masking. When PTC and MT curves 103,104 are segmented by listener age, (which is highly correlated with hearing loss as defined by PTT data 101, 102 of FIG. 1A), there is a clear trend of the broadening of PTC and/or MT curve with age, as seen in FIG. 1B.

Figure 2:
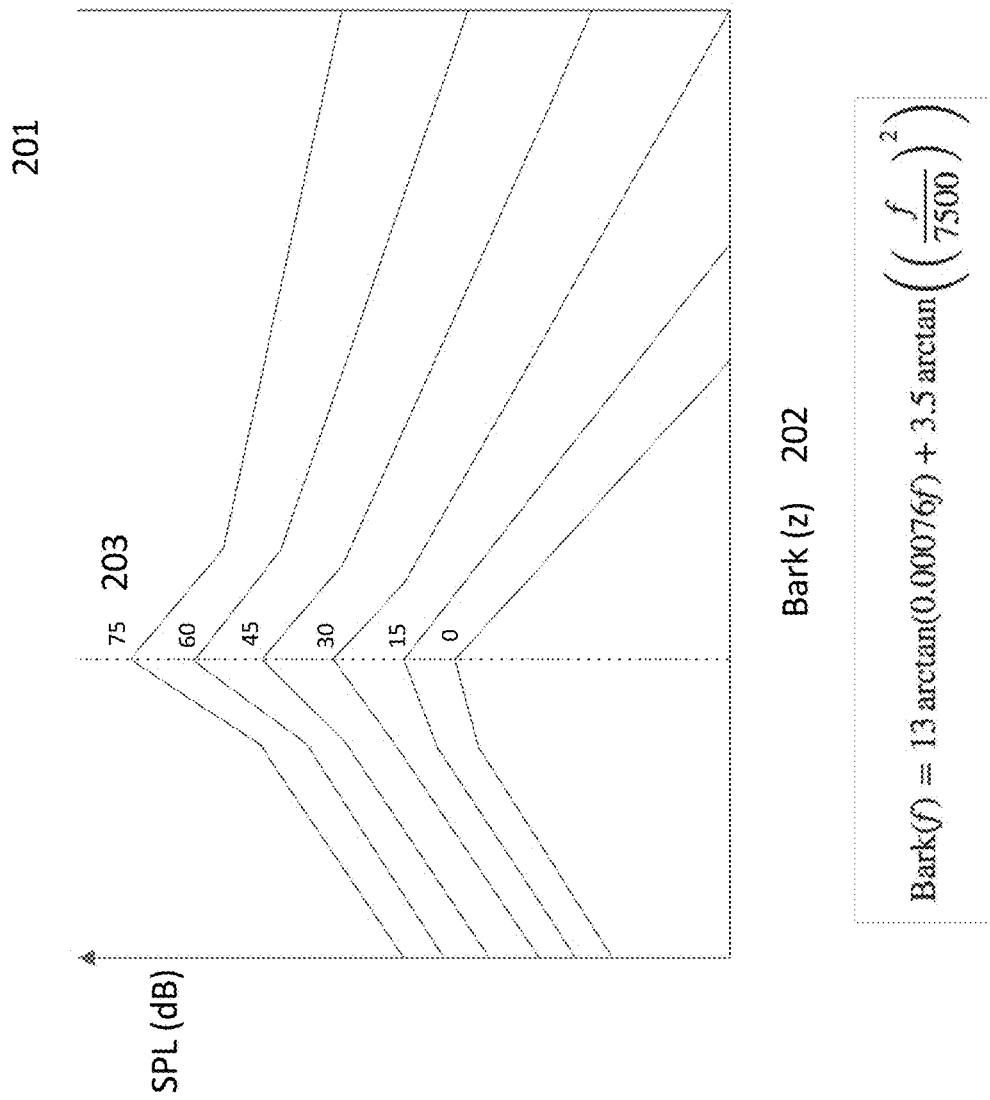
FIG. 2 illustrates a collection of prototype masking functions for a single-tone masker shown with level as a parameter.

FIG. 2 depicts example masking functions for a sinusoidal masker with sound level as the parameter 203 of the different example masking functions. Frequency is expressed according to the Bark scale, 201, 202, which is a psychoacoustical scale in which the critical bands of human hearing each have a width of one Bark (a critical band is a band of audio frequencies within which a second tone will interfere with the perception of the first tone by auditory masking). For the purposes of masking, the Bark scale provides a more linear visualization of spreading functions. As illustrated, the higher the sound level of the sinusoidal masker, the greater the amount of masking occurs across a broader expanse of frequency bands.

Figure 3:
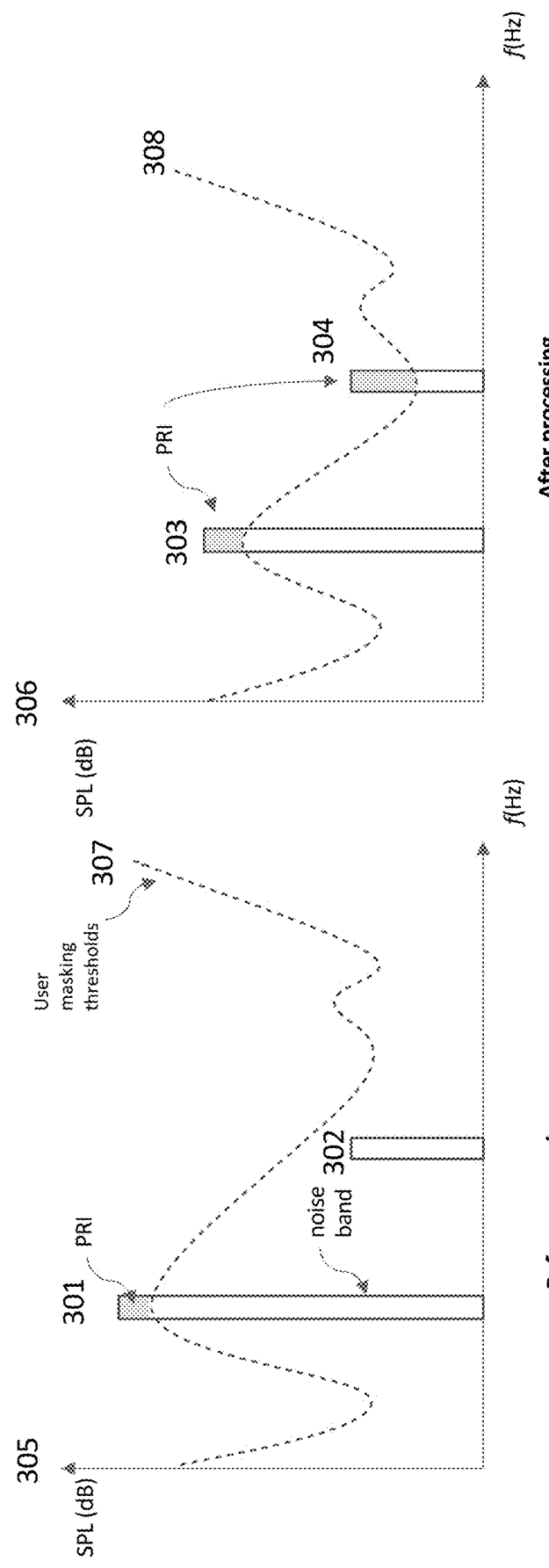
FIG. 3 illustrates an example of a simple, transformed audio signal in which compression of a masking noise band leads to an increase in PRI.

FIG. 3 illustrates a sample of a simple, transformed audio signal consisting of two narrow bands of noise, 301 and 302. In a first instance 305, before processing is performed, signal 301 masks signal 302, via masking threshold curve 307, thereby rendering signal 302 perceptually inaudible. In the second instance 306, after processing is performed, a signal component 303 is compressed, reducing its signal strength to such an extent that signal 304 is unmasked. The net result is an increase in PRI, as represented by the shaded areas 303, 304 located above the modified user masking threshold curve 308.

Figure 4:
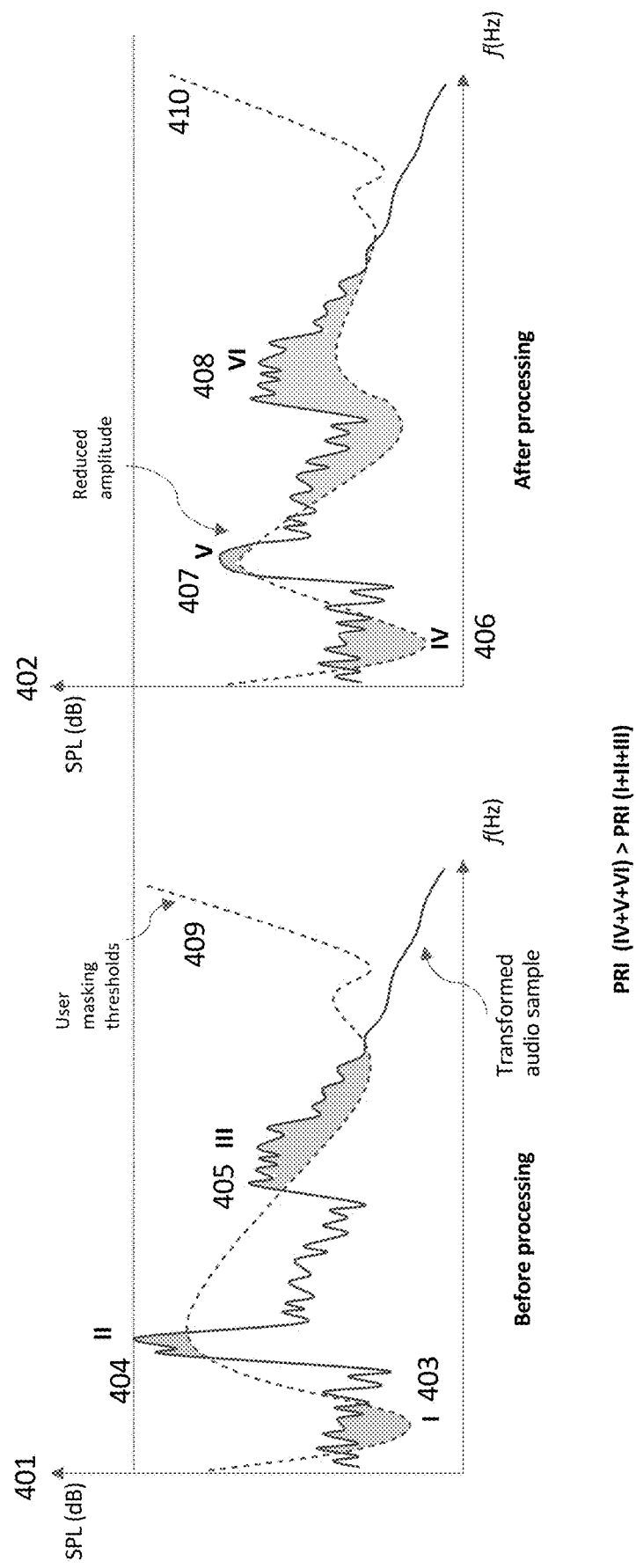
FIG. 4 illustrates an example of a more complex, transformed audio signal in which compression of a signal masker leads to an increase in PRI.
Figure 5:
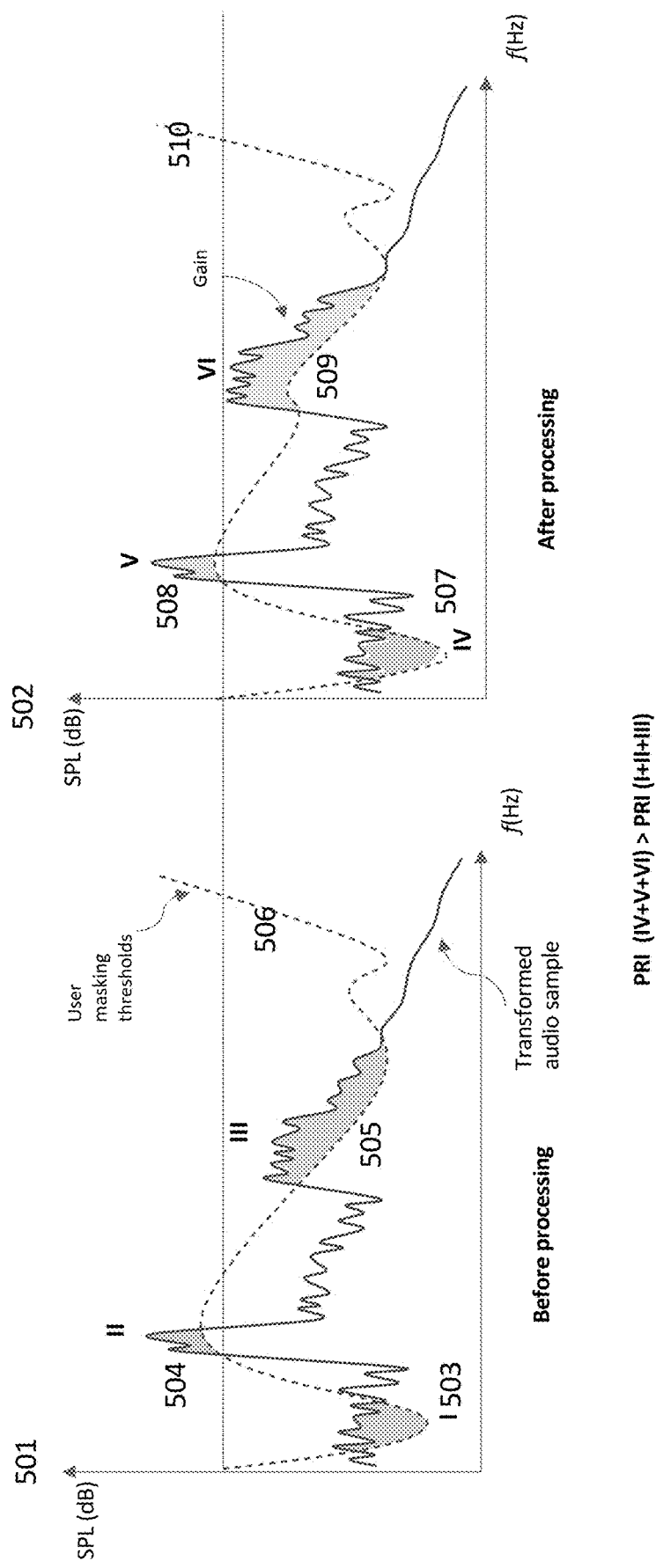
FIG. 5 illustrates an example of a complex, transformed audio signal in which increasing gain for an audio signal leads to an increase in PRI.

FIGS. 4 and 5 illustrate samples of a more complex, transformed audio signal than the simple, transformed audio signal of FIG. 3. In FIG. 4, in a first instance 401 (before processing), a masking signal component 404 masks much of audio signal 405, via a masking threshold curve 409. In a second instance 402 (after processing), through compression of signal component 404, the masking threshold curve 410 is changed and PRI increases, as represented by shaded areas 406-408 above the user making threshold curve 410. Thus, the user's listening experience improves due to this increase in PRI. Similarly, PRI may also be increased through the application of gain in specific frequency regions, as illustrated in FIG. 5. Through the application of gain to signal component 505, the corresponding signal component 509 is increased in amplitude relative to masking threshold curve 510, thus increasing user PRI. The above explanation is presented to visualize the effects of sound augmentation DSP. In general, sound augmentation DSP modifies signal levels in a frequency selective manner, e.g., by applying gain or compression to sound components to achieve the above-mentioned effects (other DSP processing that has the same effect is possible as well). For example, the signal levels of high-power (masking) sounds (frequency components) are decreased through compression to thereby reduce the masking effects caused by these sounds, and the signal levels of other signal components are selectively raised (by applying gain) above the hearing thresholds of the listener.

PRI can be calculated according to a variety of methods, as would be appreciated by one of ordinary skill in the art. One such method, called perceptual entropy, was developed by James D. Johnston at Bell Labs, and generally comprises: transforming a sampled window of audio signal into the frequency domain, obtaining masking thresholds using psychoacoustic rules by performing critical band analysis, determining noise-like or tone-like regions of the audio signal, applying thresholding rules for the signal and then accounting for absolute hearing thresholds. Following this, the number of bits required to quantize the spectrum without introducing perceptible quantization error is determined. For instance, Painter & Spanias disclose the following formulation for perceptual entropy in units of bits/s, which is closely related to ISO/IEC MPEG-1 psychoacoustic model 2 [Painter & Spanias, *Perceptual Coding of Digital Audio*, Proc. Of IEEE, Vol. 88, No. 4 (2000); see also generally Moving Picture Expert Group standards (mpeg.chiariglione.org)]:

$$PE = \sum_{i=1}^{25} \sum_{\omega}^{bh_i} \log_2 \left( 2 \left| nint\left( \frac{Re(\omega)}{\sqrt{6T_i/k_i}} \right) + 1 \right| \right) + \log_2 \left( 2 \left| nint\left( \frac{Im(\omega)}{\sqrt{6T_i/k_i}} \right) + 1 \right| \right) \quad \text{(Eq. 1)}$$

Where:
i=index of critical band;
$bl_i$ and $bh_i$=upper and lower bounds of band i;
$k_i$=number of transform components in band i;
$T_i$=masking threshold in band i;
nint=rounding to the nearest integer;
$Re(\omega)$=real transform spectral components; and
$Im(\omega)$=imaginary transform spectral components.

Figure 6:
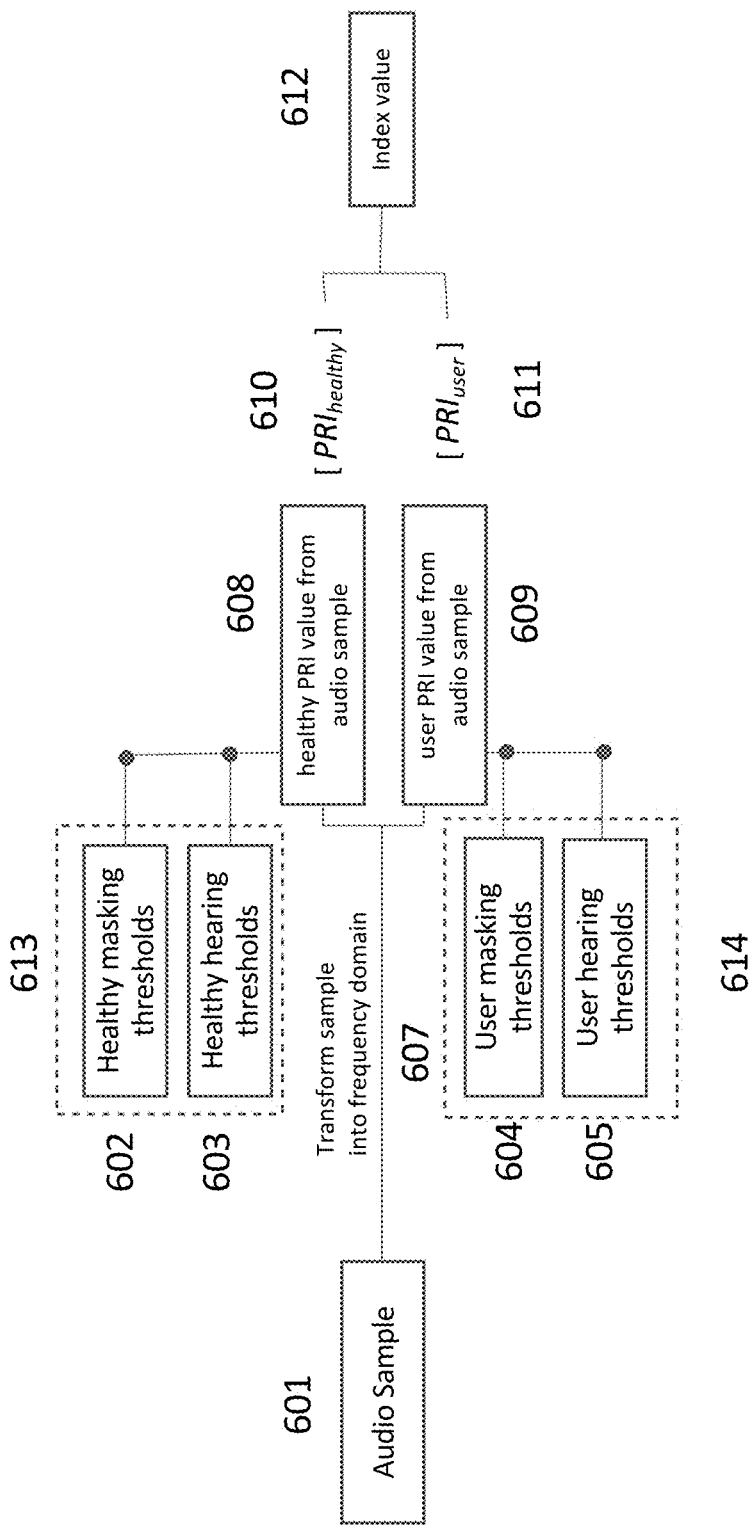
FIG. 6 illustrates a flow chart detailing the method of calculating hearing health from a healthy, standard PRI value and a custom, listener PRI value.

FIG. 6 illustrates an example process of the present disclosure, in which a user's hearing health may be derived from an audio sample. In particular, a user's hearing health can be obtained by analyzing the PRI values from a healthy, standardized hearing profile 613 against the values from the user's hearing profile 614. First, standardized (healthy) hearing profiles 613 and the user's hearing profile 614 are obtained and individual masking thresholds 602, 604 and hearing thresholds 603, 605 are determined. One or more of the hearing thresholds 603, 604 may readily be determined from audiogram data. One or more of masking thresholds 602, 604 may also readily be determined from masking threshold curves, as discussed above. In some embodiments, hearing thresholds 603, 605 may additionally be obtained from results from masking threshold curves (as described in commonly owned EP17171413.2, entitled "Method for accurately estimating a pure tone threshold using an unreferenced audio-system"). Subsequently, masking threshold 602, 604 and hearing thresholds 603, 605 are applied to a transformed audio sample 607 (which is obtained by transforming an input audio sample 601 into the frequency domain, e.g., using a fast Fourier Transform (FFT)), in order to thereby generate a healthy standard PRI value 608, 610 and a user PRI value 609, 611. These PRI values may then be used to create a PRI index value 612, such as a ratio value calculated as [$PRI_{user}$]/[$PRI_{healthy}$].

The approach described above with respect to FIG. 6 provides the benefits of integrating complex suprathreshold and threshold data across the audible spectrum into a singular, objective value that can be readily compared to a standardized healthy value for a given audio sample 601. It further allows a user to get a more facile understanding of hearing loss by displaying the value of perceptual loss for many different given audio samples 601—whether the audio sample is an individual song, recorded speech content, a music genre, a series of podcasts, or an entire corpus of audio, etc. For example, a user may be apprised that they have greater perceptual loss for classical music, which typically features a wider dynamic range and higher harmonics. Or, a user may record speech in an everyday listening situation—such as in a noisy bar—to examine how much perceptual loss he or she experiences or perceives relative to what a healthy ear would experience or perceive.

Figure 7:
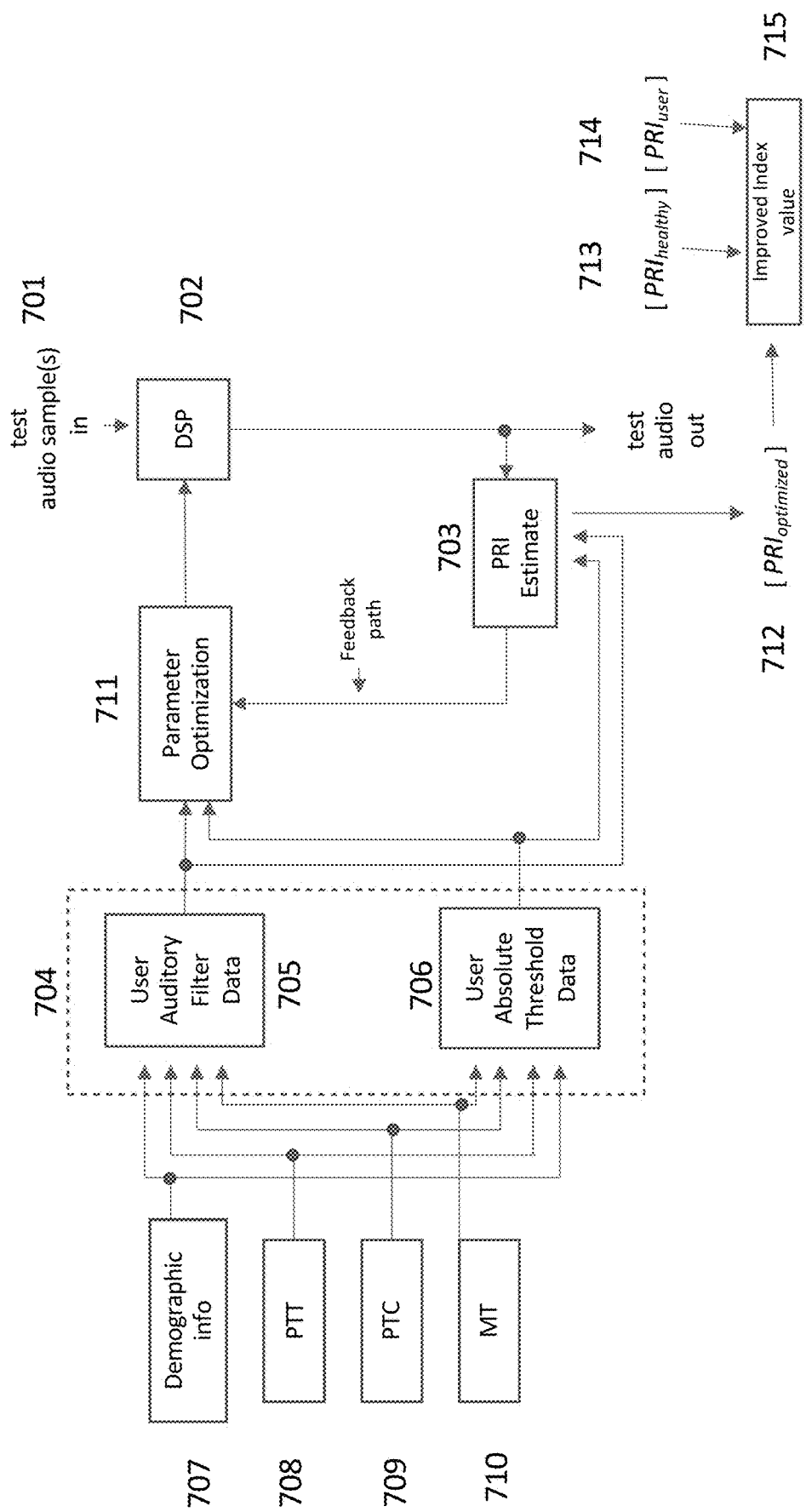
FIG. 7 illustrates a flow chart detailing a PRI approach to parameter optimization in which an optimized PRI value is generated.

FIG. 7 demonstrates an additional benefit of using PRI measures to convey hearing health as users can gauge the perceptual rescue effects offered by sound personalization DSPs and/or hearing aid systems that have been optimally parameterized by PRI calculations. An audio sample, or body of audio samples, 701 is first processed by a parameterized multiband dynamics processor (DSP) 702 and the PRI of the processed output signal(s) is calculated 703 according to a hearing profile 704 of the user. The hearing profile 704 itself bears the masking and hearing thresholds of the particular user. Hearing profile 704 may be derived from one or more sources which include, but are not limited to, the user's demographic info 707, the user's PTT data 708, the user's PTC data 709, the user's MT data 710, a combination of these, or optionally from other sources. After the PRI calculation 703 is performed, the multiband dynamic processor 702 is re-parameterized according to a given set of parameter heuristics, derived from a parameter optimization 711. From parameter optimization 711 (and the associated re-parameterization of DSP 702), the audio sample(s) 701 reprocessed and the PRI calculated.

In other words, the multiband dynamics processor 702 is configured to process the audio sample 701 such that audio sample 701 has an increased PRI for the particular listener (i.e., the user), taking into account the individual listener's personal hearing profile 704. To this end, parameterization of the multiband dynamics processor 702 is adapted to increase the PRI of the processed audio sample over the unprocessed audio sample. As mentioned previously, the parameters of the multiband dynamics processor 702 are determined by an optimization process 711 that uses PRI as its optimization criterion. The above approach for processing an audio signal based on optimizing PRI and taking into account a listener's hearing characteristics may be based not only on multiband dynamic processors, but also on any kind of parameterized audio processing function that can be applied to the audio sample 701 and its parameters determined so as to optimize PRI of the audio sample. A [$PRI_{optimized}$] value 712 is then outputted, which then can be analyzed against [$PRI_{user}$] 713 and [$PRI_{healthy}$] 714 to generate an improved PRI index value 715 for the user.

The parameters of the audio processing function may be determined for an entire audio file, for a corpus of audio files, or separately for portions of an audio file (e.g. for specific frames of the audio file). The audio file(s) may be analyzed before being processed, played or encoded. Processed and/or encoded audio files may be stored for later usage by the particular listener (e.g. in the listeners audio archive). For example, an audio file (or portions thereof) encoded based on the listener's hearing profile may be stored or transmitted to a far-end device such as an audio communication device (e.g. telephone handset) of the remote party. Alternatively or additionally, an audio file (or portions thereof) processed using a multiband dynamic processor that is parameterized according to the listener's hearing profile may be stored or transmitted.

Various optimization methods are possible to maximize the PRI of an audio sample, depending on the type of the applied audio processing function. For example, a subband dynamic compressor may be parameterized by compression threshold, attack time, gain and compression ratio for each subband, and these parameters may be determined by the optimization process. In some cases, the effect of the multiband dynamics processor on the audio signal is nonlinear and an appropriate optimization technique is required to account for the nonlinearity. The number of parameters that need to be determined may become large, e.g., if the audio signal is processed in many subbands and a plurality of parameters needs to be determined for each subband of the many subbands. In such cases, it may not be practicable to optimize all parameters simultaneously and a sequential approach to parameter optimization may be applied. Various approaches for sequential optimization are disclosed below. Although these sequential optimization procedures do not necessarily result in the optimum parameters, the obtained parameter values result in increased PRI over the unprocessed audio sample and thereby improve the user's listening experience.

A brute force approach to multi-dimensional optimization of processing parameters may be based on trial and error and successive refinement of a search grid. First, a broad search range is determined based on some a priori expectation on where an optimal solution might be located in the parameter space. Constraints on reasonable parameter values may be applied to limit the search range. Then, a search grid or lattice having a coarse step size is established in each dimension of the parameter space. One should note that the step size need not be constant but may, in some embodiments, differ across one or more of the processing parameters. For example, a compression threshold may be searched between 50 and 90 dB, in steps of 10 dB; simultaneously, a compression ratio between 0.1 and 0.9 may be searched in steps of 0.1. Thus, the search grid of this example has 5×9=45 points. PRI is determined for each parameter combination associated with a search point of the search grid, and the maximum PRI for the search grid is determined. The search may then be repeated in a next iteration, starting with the parameters that previously yielded the best (i.e., maximum) result of the prior iteration, and using a reduced range and step size. For example, a compression threshold of 70 dB and a compression rate of 0.4 were determined to have maximum PRI in the first search grid. Then, a new search range for thresholds between 60 dB and 80 dB and for ratios between 0.3 and 0.5 may be set for the next, second, iteration. The step sizes for the next optimization may be determined to 2 dB for the threshold and 0.05 for the ratio, and the combination of parameters having maximum PRI for the search grid of the second iteration determined. Further iterations may be performed for refinement. Other and additional parameters of the signal processing function may be considered as well. In the case of a multiband compressor, parameters for each subband must be determined. Simultaneously searching optimum parameters for a larger number of subbands may, however, take a long time or even become unfeasible. Thus, the present disclosure suggests various ways of structuring the optimization in a sequential manner to perform the parameter optimization in a shorter time without losing an unacceptable amount of precision in the search. The disclosed approaches are not limited to the above brute force search but may be applied to other optimization techniques as well.

Figure 8:
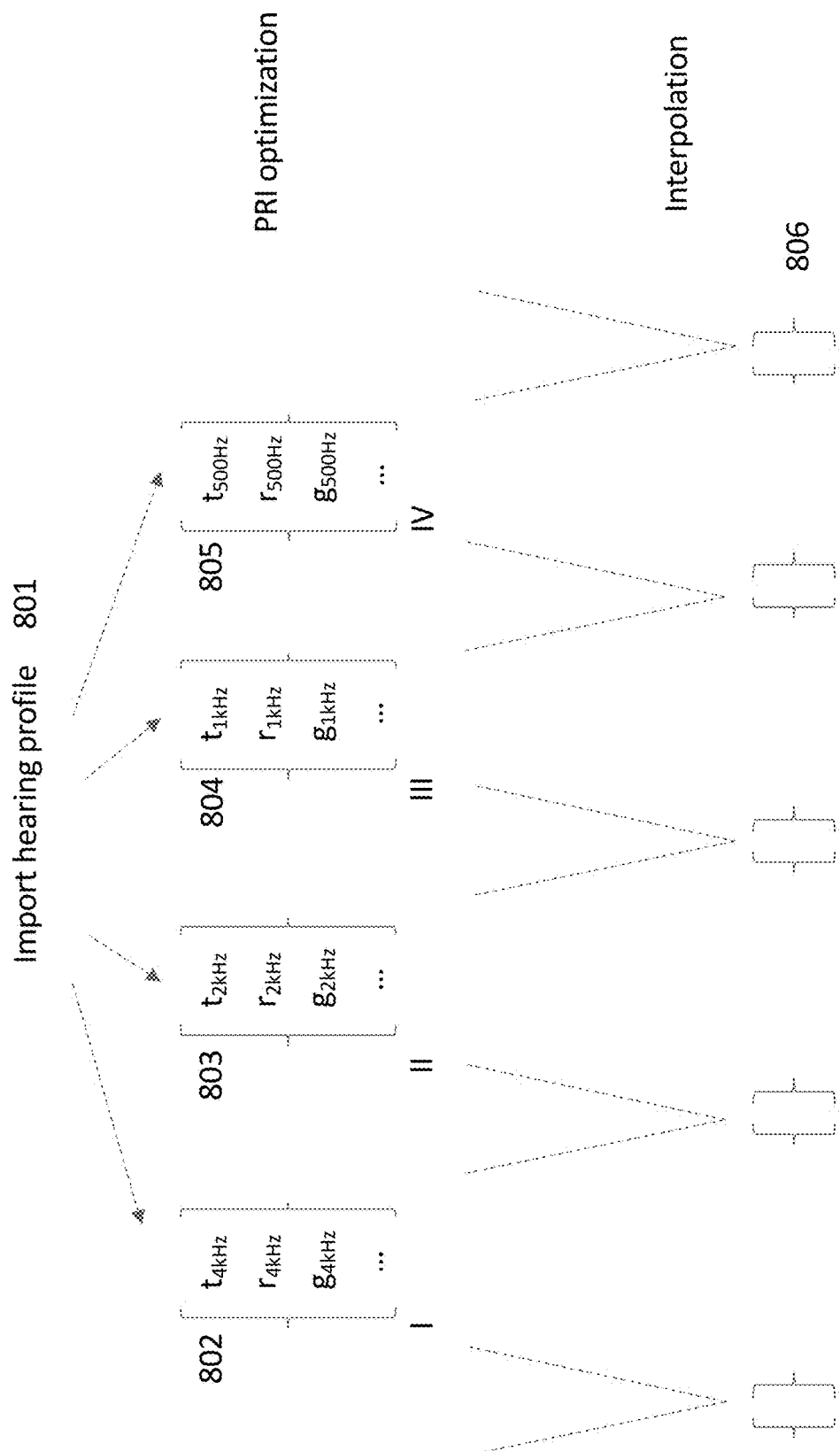
FIG. 8 illustrates one method of PRI optimization amongst subbands in a multiband dynamic processor.

As illustrated in FIG. 8, one mode of optimization may be performed by first optimizing subbands successively around available psychophysical tuning curve (PTC) data 801 in non-interacting subbands, i.e., a band of sufficient distance where off-frequency masking does not occur between them. For instance, the results of a 4 kHz PTC test 801 are first imported and optimization at 4 kHz is performed to maximize PRI for this subband by adjusting compression thresholds $t_i$, gains $g_i$ and ratios $r_i$ 802. Successive octave bands are then optimized, around 2 kHz (803), 1 kHz (804) and 500 Hz (805). After this is performed, the parameters of the remaining subbands can then be interpolated at 806. Additionally, imported PTC results 801 can be used to estimate PTC and audiogram data at other frequencies, such as at 8 kHz, following which the 8 kHz subband can be optimized accordingly.

Figure 10:
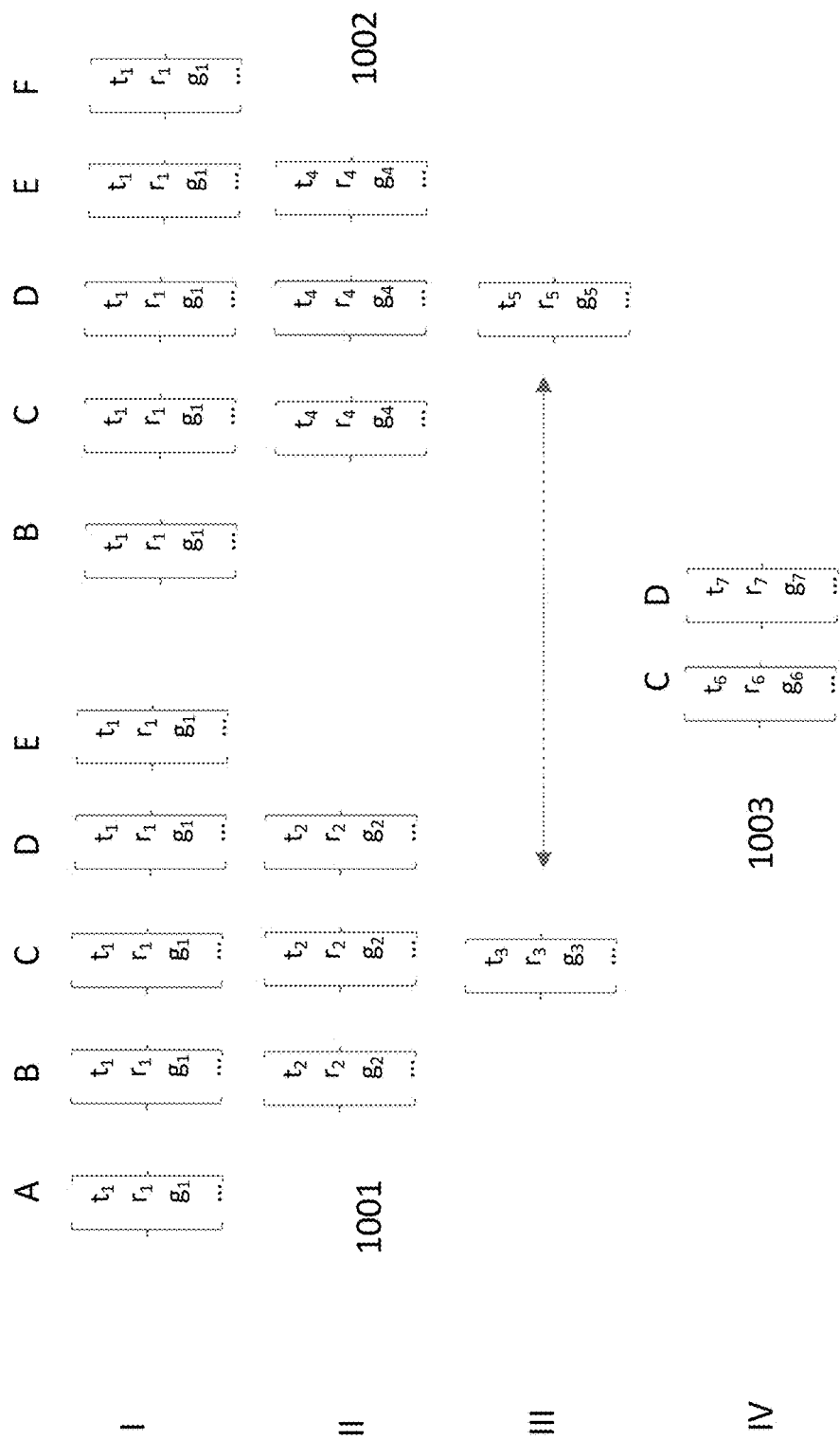
FIG. 10 illustrates a further refinement of the method illustrated in FIG. 9.

Another optimization approach is illustrated in FIG. 10. This approach first optimizes around the same parameter values fixed amongst a plurality of (e.g., every) subbands 1001. In this instance, the compression threshold and ratios would be identical in all subbands, but the values adjusted so as to optimize PRI. Successive iteration would then granularize the approach 1002, 1003—keeping the parameters tied amongst subbands but narrowing down the number of subbands that are being optimized simultaneously until finally optimizing one individual subband. The results of the optimization of the previous step could be used as a starting point for the current optimization across fewer subbands. In addition, in some embodiments it may be possible to adjust other optimization parameters for a more precise optimization around the starting point. For example, the step size of a search for optimal parameter values might be reduced. The process would then be iterated with a new initial set of subbands and successive reduction of considered subbands so as to find a solution for each subband. Once each subband is optimized, their individual parameters may be further refined by again optimizing adjacent bands. For example, parameters of adjacent bands may be averaged or filtered (on a parameter type by parameter type basis, e.g. filtering of thresholds) so as to obtain a smoother transition of parameters across subbands. Missing subband parameters may be interpolated.

Figure 9:
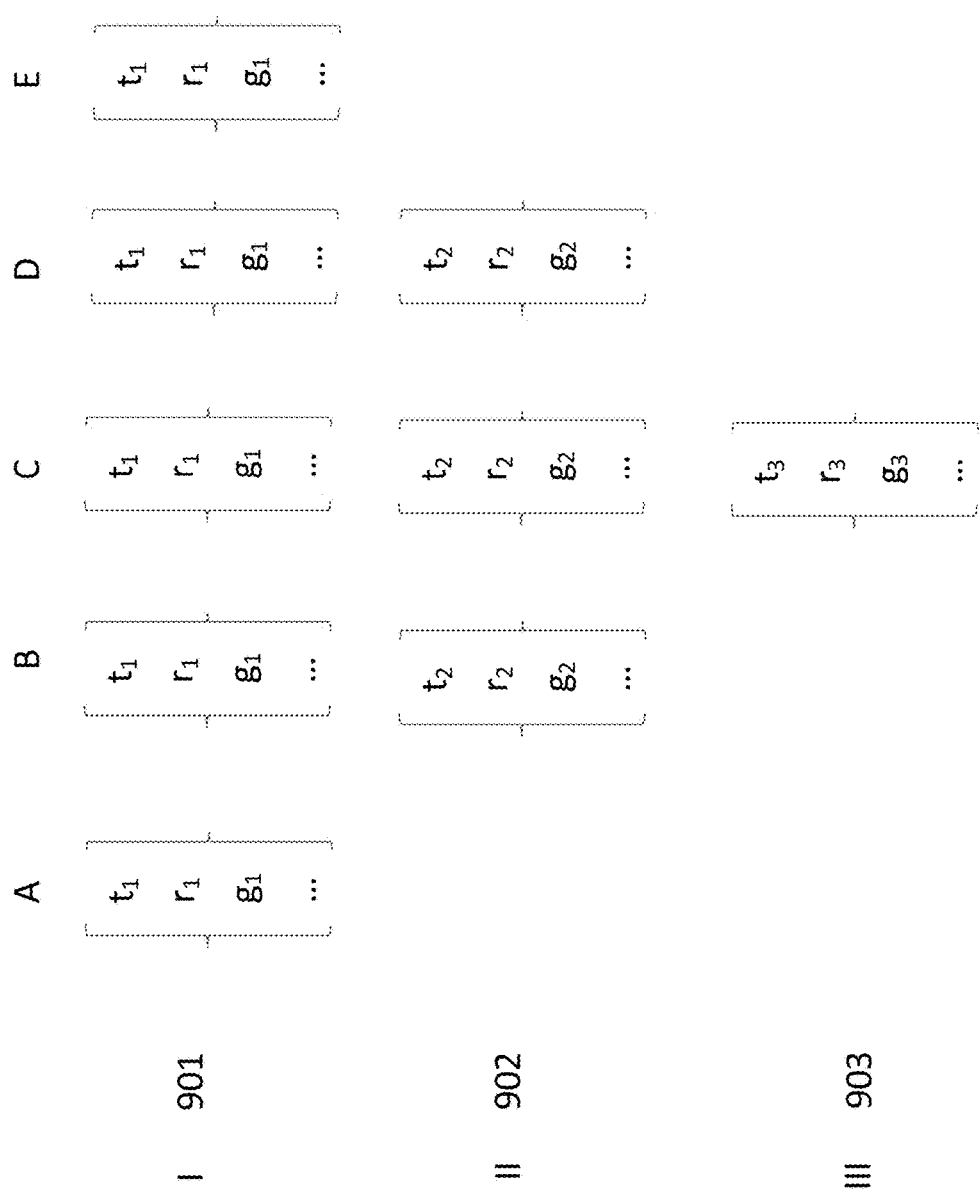
FIG. 9 illustrates another method of PRI optimization, wherein optimization is increasingly granularized.

For example, in FIG. 9, subbands A-E are optimized to determine parameters 901 [$t_1$, $r_1$, $g_1$, . . . ] for compression threshold $t_1$, ratio $r_1$ and gain $g_1$. Other or additional parameters may be optimized without departing from the scope of the present disclosure. Next, subbands B, C and D are optimized to determine new parameters 902 [$t_2$, $r_2$, $g_2$, . . . ] from the previously obtained parameters 901 [$t_1$, $r_1$, $g_1$, . . . ]. Finally, subband C is optimized to determine new parameters 903: [$t_3$, $r_3$, $g_3$, . . . ] from parameters 902 [$t_2$, $r_2$, $g_2$, . . . ]. As mentioned above, the previously obtained parameters may be used as a starting point for the subsequent optimization step. The approach seeks to best narrow down the optimal solution per subband by starting with fixed values across many subbands. The approach can be further refined, as illustrated in FIG. 10. Here, subbands C and D are optimized according to the approach in FIG. 9, resulting in parameters 1001 for subband C: [$t_3$, $r_3$, $g_3$, . . . ] and parameters 1002 for subband D: [$t_5$, $r_5$, $g_5$, . . . ]. Subsequently, the adjacent bands are then optimized together, resulting in refined parameters 1003 for subbands C: [$t_6$, $r_6$, $g_6$, . . . ] and D: [$t_7$, $r_7$, $g_7$, . . . ].

Figure 11:
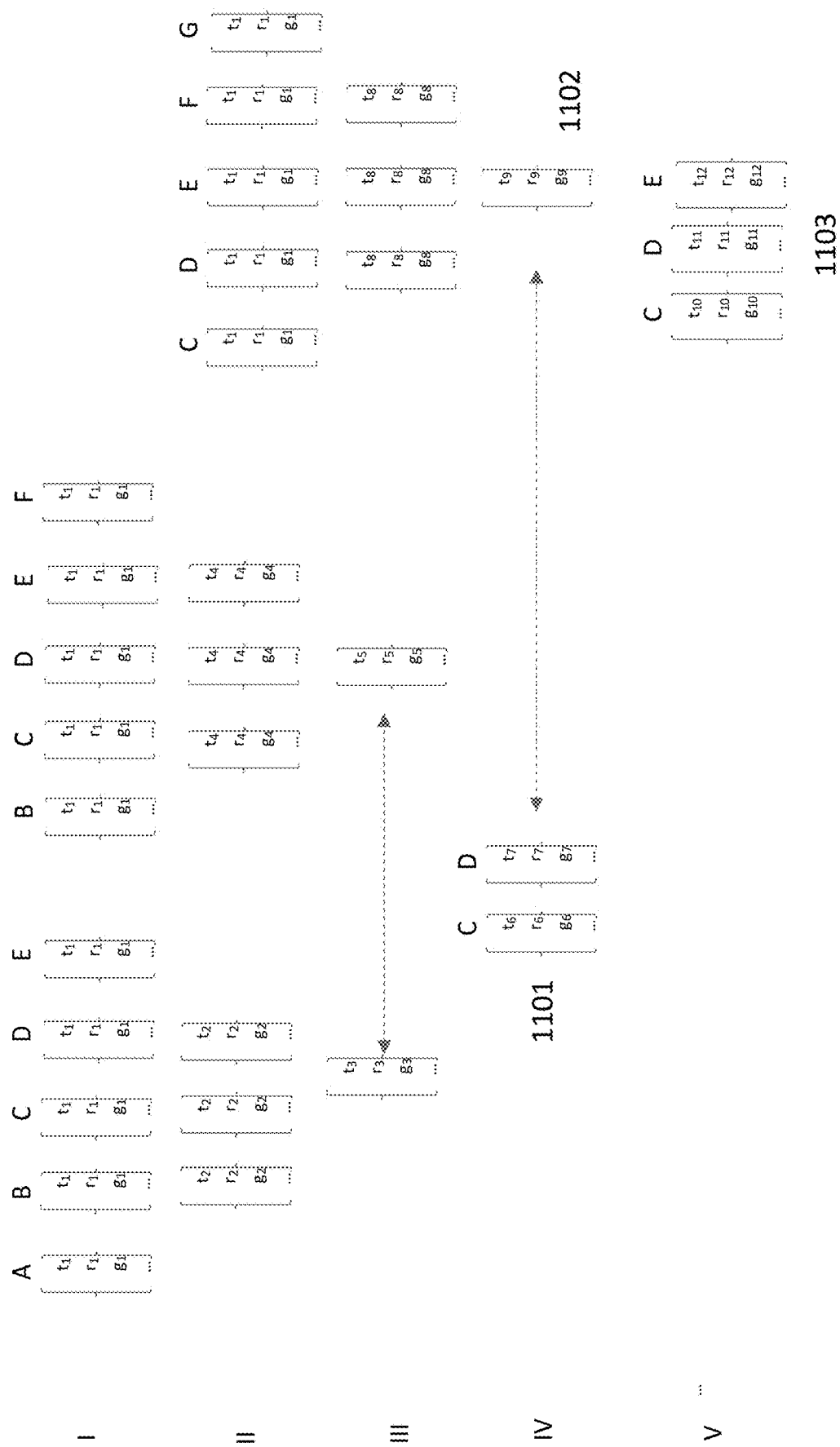
FIG. 11 illustrates further refinement of the method illustrated in FIG. 10.

In some embodiments, this optimization could be continued and taken a step further, as illustrated in FIG. 11, where subbands C and D (with parameters 1101 corresponding to parameters 1003 obtained for subbands C and D in FIG. 10) are optimized with a previously optimized subband E having parameters 1102: [$t_9$, $r_9$, $g_9$, . . . ], thus resulting in new parameter set 1103: for subband C: [$t_{10}$, $r_{10}$, $g_{10}$, . . . ], subband D: [$t_{11}$, $r_{11}$, $g_{11}$, . . . ], and subband E: [$t_{12}$, $r_{12}$, $g_{12}$, . . . ]. The main consideration in both approaches is strategically constraining parameter values—methodically optimizing subbands in a way that takes into account the functional processing of the human auditory system while narrowing the universe of possibilities. This comports with critical band theory. As mentioned previously, a critical band relates to the band of audio frequencies within which an additional signal component influences the perception of an initial signal component by auditory masking. These bands are broader for individuals with hearing impairments—and so optimizing first across a broader array of subbands (i.e. critical bands) will better allow an efficient calculation approach.

Figure 12:
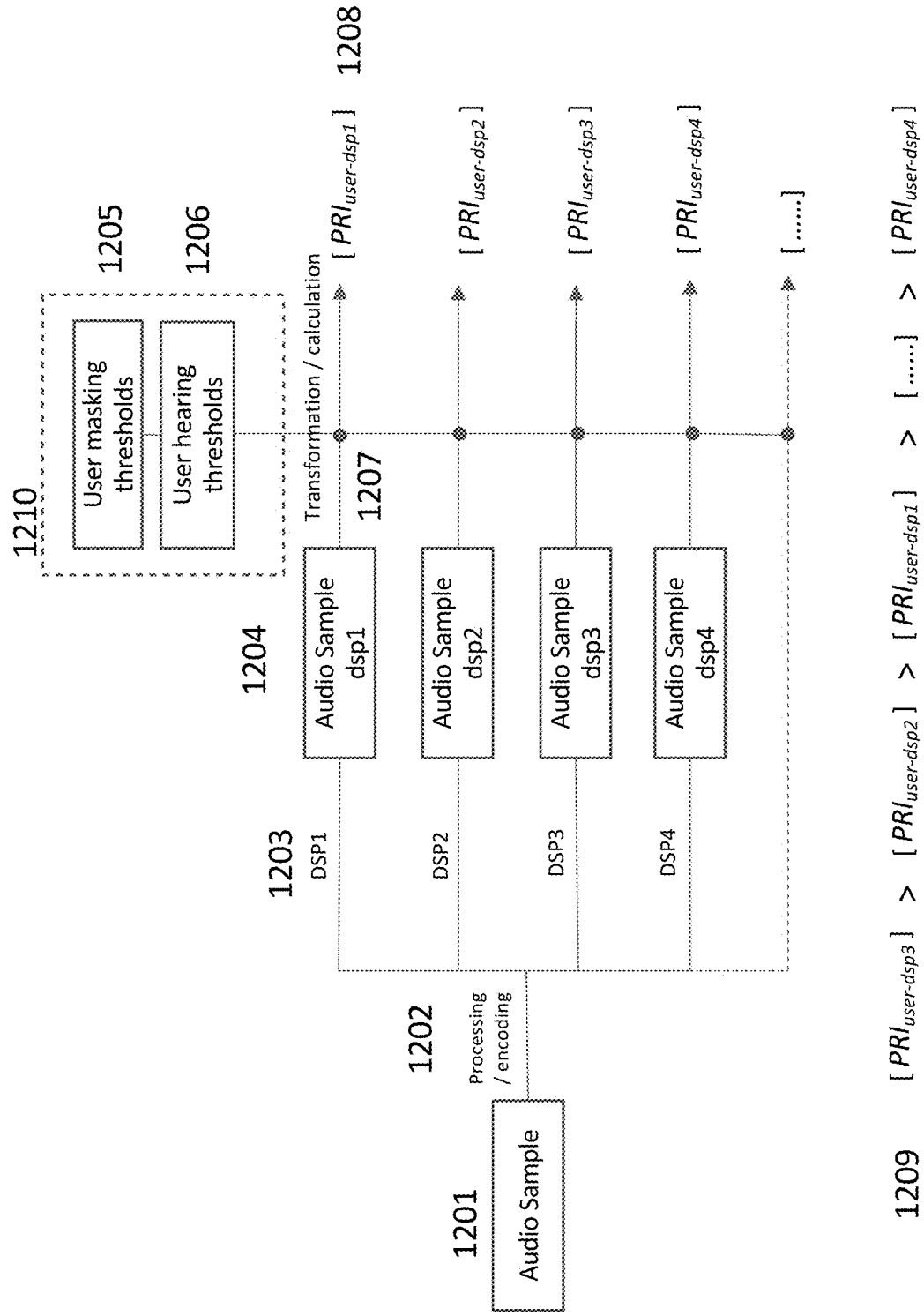
FIG. 12 illustrate a flow chart detailing how PRI values may be used to assess perceptual improvements offered by various DSP systems.

FIG. 12 illustrates a further method of using a PRI approach for evaluating hearing health to the extent of allowing a user or listener to measure the efficacy of various DSP systems. These DSP systems may optionally comprise different sound personalization DSPs, different hearing aid DSPs, differently parameterized versions of the same DSP, including DSP systems that have been optimally parameterized by PRI calculations, or any combination of the above. Similar to FIG. 6, an audio sample 1201 is processed 1202 by each DSP 1203 into a separately processed audio sample 1204 and transformed 1207. A user's hearing profile, 1210, comprising masking thresholds 1205 and hearing thresholds 1206, is applied to each transformed audio sample 1207 and a DSP-specific PRI score 1208 is generated. To this extent, a given user or listener can more accurately evaluate the perceptual rescue offered by various DSP systems 1209 using one objective criteria—the PRI score 1208.

In the following discussion of FIG. 13, a method is disclosed for deriving a pure tone threshold from a psychophysical tuning curve using an uncalibrated audio system. This allows the determination of a user's hearing profile without requiring a calibrated test system. For example, the tests to determine the PTC of a listener and his/her hearing profile can be performed at the user's home using his/her personal computer, tablet computer, or smartphone, etc. A hearing profile that is determined in this way can then be used in conjunction with one or more of the above audio processing techniques to increase coding efficiency for an audio signal or to improve the user's listening experience by selectively processing (frequency) bands of the audio signal to increase PRI.

Figure 13:
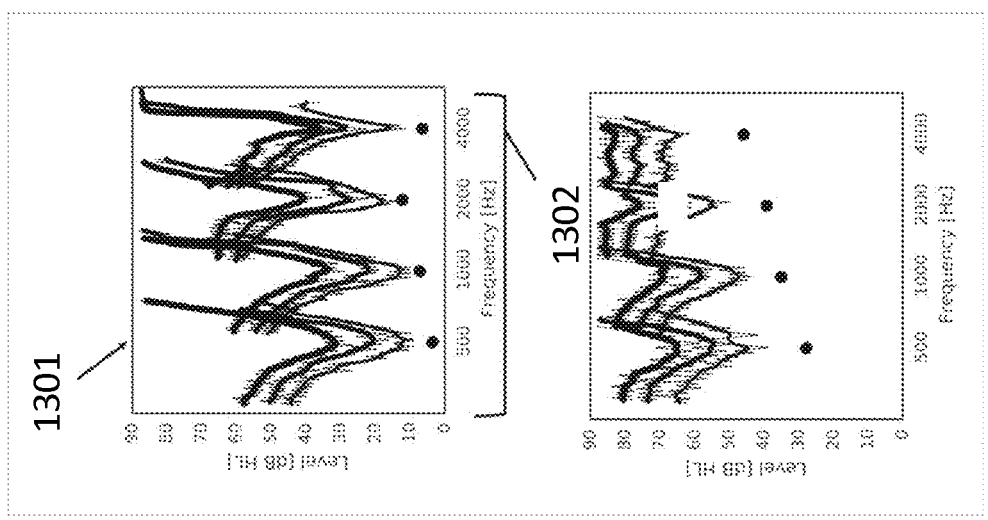
FIG. 13 shows PTC test results acquired on a calibrated setup in order to generate a training set.

FIG. 13 illustrates test results acquired with a calibrated setup in order to generate a training set for training of a classifier that predicts pure-tone thresholds based on PTC features of an uncalibrated setup. The classifier may be provided as, for example, a linear regression model. Therefore, the acquired PTC tests can be given in absolute units such as dB HL. However, this is not crucial for the further evaluation. In the present example, four PTC tests at different signal tone frequencies (500 Hz, 1 kHz, 2 kHz and 4 kHz) and at three different sound levels (40 dB HL, 30 dB HL and 20 dB HL indicated by line weight; the thicker the line the lower the signal tone level) for each signal tone have been performed. Therefore, at each signal tone frequency, there are three PTC curves. The PTC curves each are essentially V-shaped. Dots below the PTC curves indicate the results from a calibrated—and thus absolute—pure tone threshold test performed with the same test subject. On the upper panel 1301, the PTC results and pure tone threshold test results acquired from a normal hearing person are shown (versus the frequency 1302), wherein on the lower panel, the same tests are shown for a hearing-impaired ("HI") person. In the example shown, a training set comprising 20 persons, both normal hearing and hearing-impaired persons, was acquired to generate the results.

Figure 14:
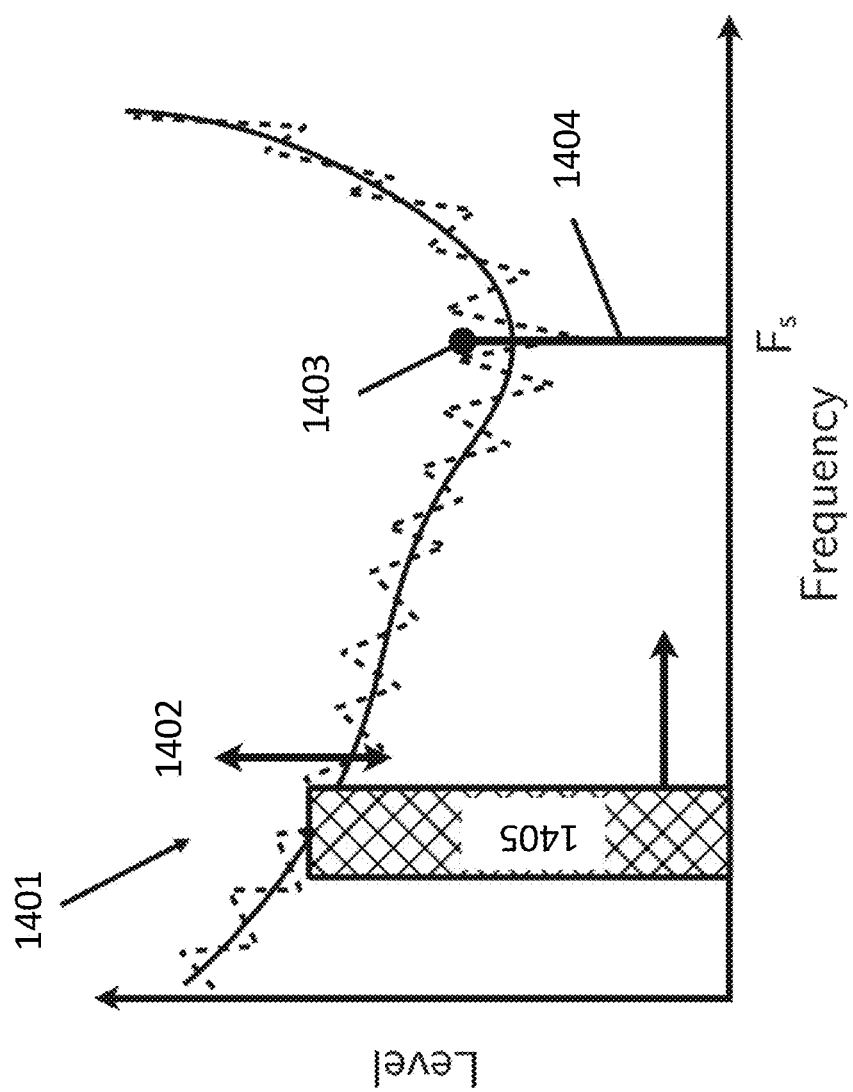
FIG. 14 shows an illustration of a PTC measurement.

FIG. 14 depicts an illustration of a PTC measurement. A signal tone 1403 is masked by a masker signal 1405, particularly when sweeping a frequency range in the proximity of the signal tone 1403. The test subject indicates at which sound level he/she hears the signal tone for each masker signal. The signal tone and the masker signal are well within the hearing range of the test subject (i.e., the user or listener). The diagram shows on the x-axis the frequency and on the y-axis the audio level or intensity in arbitrary units. While a signal tone 1403 that is constant in frequency and intensity 1404 is played to the test subject, masker signal 1405 slowly sweeps from a frequency lower than signal tone 1403 to a frequency higher than signal tone 1403. The rate of sweeping is constant or can be controlled by the test subject or the operator. The goal for the test subject is to hear the signal tone 1403. When the test subject does not hear the signal tone 1403 anymore (which can be indicated by the test subject releasing a push button), the masker signal intensity 1402 is reduced to a point where the test subject once again starts hearing the signal tone 1403 (which can be indicated by the test subject by pressing the push button).

While the masker signal tone 1405 is still sweeping upwards in frequency, the intensity 1402 of masker signal 1405 is then increased again, until the test subject no longer hears signal tone 1403. In this manner, the masker signal intensity 1402 oscillates around the hearing level 1401 (as indicated by the solid line) of the test subject with regard to the masker signal frequency and the signal tone. This hearing level 1401 is well established and well known for people having no hearing loss. Any deviations from this curve indicate a hearing loss (see for example FIG. 15).

Figure 15:
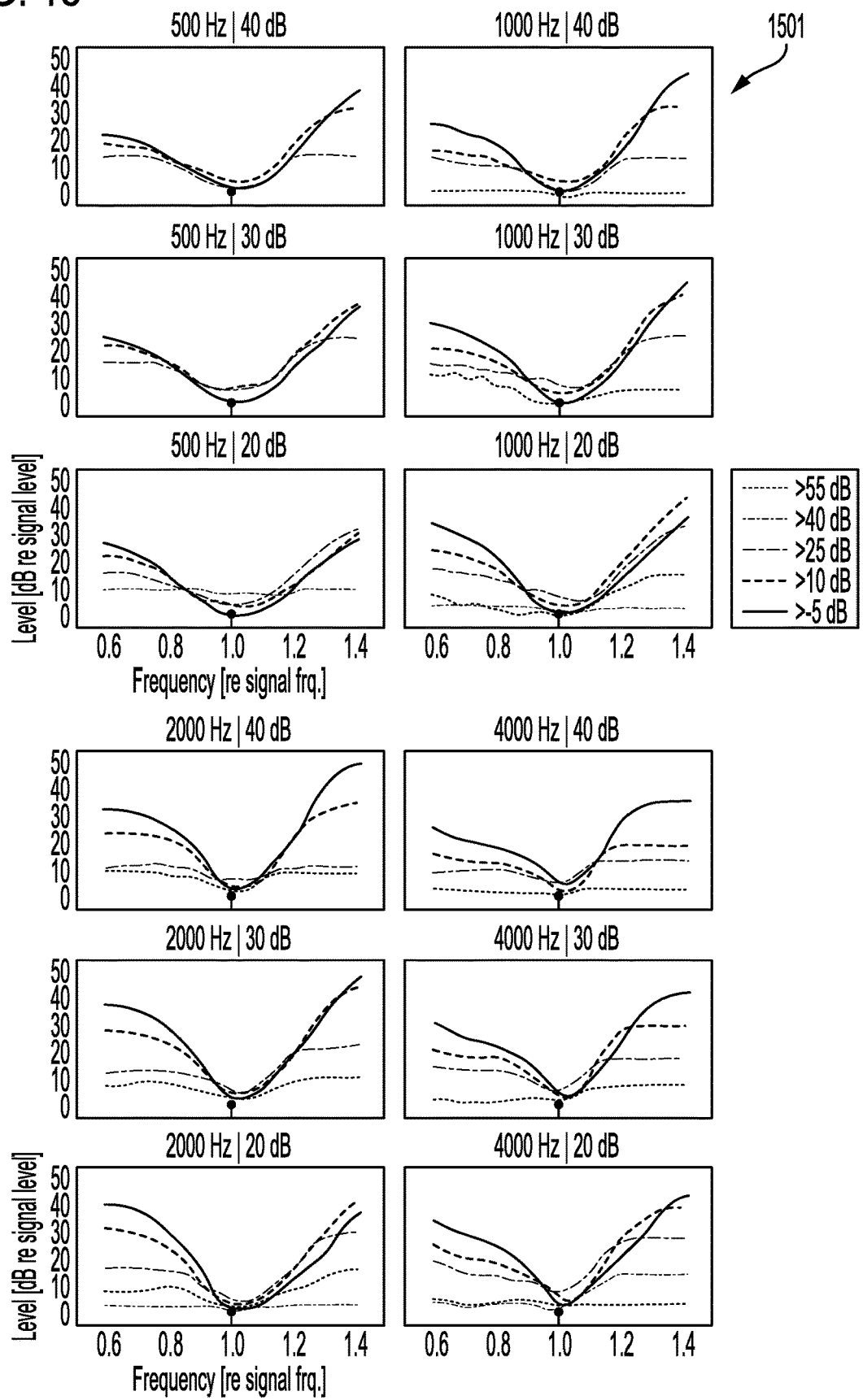
FIG. 15 shows a summary of PTC test results.

In FIG. 15 a summary of PTC test results 1501 of a training set are plotted. The plots are grouped according to single tone frequency and sound level resulting in 12 panels or plots. In each panel, the PTC results are grouped in 5 groups (indicated by different line styles), according to their associated pure tone threshold test result. In some panels pure tone thresholds were not available, so these groups could not be established. The groups comprise the following pure tone thresholds indicated by line illustration style: thin dotted line: >55 dB; thick dotted line: >40 dB; dash-dot line: >25 dB; dashed line: >10 dB; and continuous line: >−5 dB. The PTC curves have been normalized relative to signal frequency and sound level for purposes of comparison. Therefore, the x-axis is normalized with respect to the signal tone frequency. The x-axes and y-axes of all plots show the same range. As can easily be discerned across all graphs, elevations in threshold gradually coincide with wider PTCs, i.e. hearing impaired (HI) listeners have progressively broader tuning compared to normal hearing (NH) subjects. This qualitative observation can be used for quantitatively determining at least one pure tone threshold from the shape-features of the PTC. Modelling of the data may be realized using a multivariate linear regression function of individual pure tone thresholds against corresponding PTCs across listeners, with separate models fit for each experimental condition (i.e. for each signal tone frequency and sound level). To capture the dominant variabilities of the PTCs across listeners—and in turn reduce dimensionality of the predictors, i.e., to extract a characterizing parameter set—PTC traces are subjected to a principle component analysis (PCA). Including more than the first five PCA components does not improve predictive power.

Figure 16:
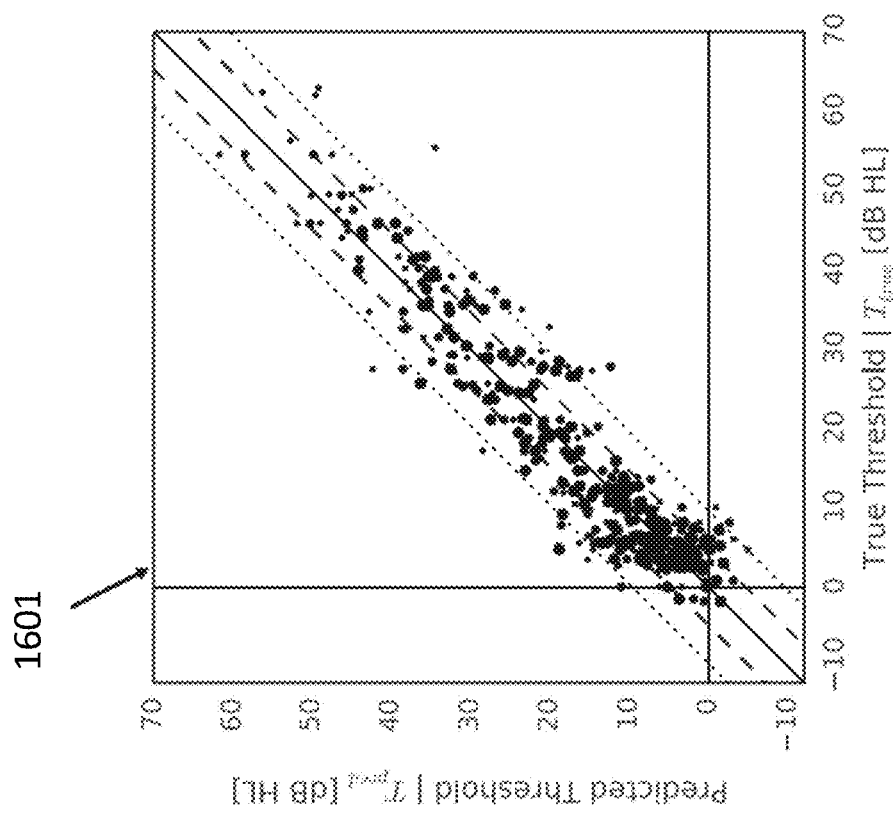
FIG. 16 summarizes fitted models' threshold predictions.

FIG. 16 summarizes the fitted models' threshold predictions. Across all listeners and conditions, the standard absolute error of estimation amounted to 4.8 dB and 89% of threshold estimates were within a standard 10 dB variability. Plots of regression weights across PTC masker frequency indicate that mostly low-frequency, but also high-frequency regions of a PTC trace are predictive of corresponding thresholds. Thus, with the generated regression function of the present disclosure, it is possible to determine an absolute pure tone threshold from an uncalibrated audio system, and in particular, the shape-feature of the PTC can be used to conclude from a PTC of unknown absolute sound level to the absolute pure tone threshold. FIG. 16 depicts a graph 1601 of the PTC-predicted vs. true audiometric pure tone thresholds across all listeners and experimental conditions (marker size indicates the PTC signal level). Dashed (dotted) lines represent unit (double) standard error of estimate.

Figure 17:
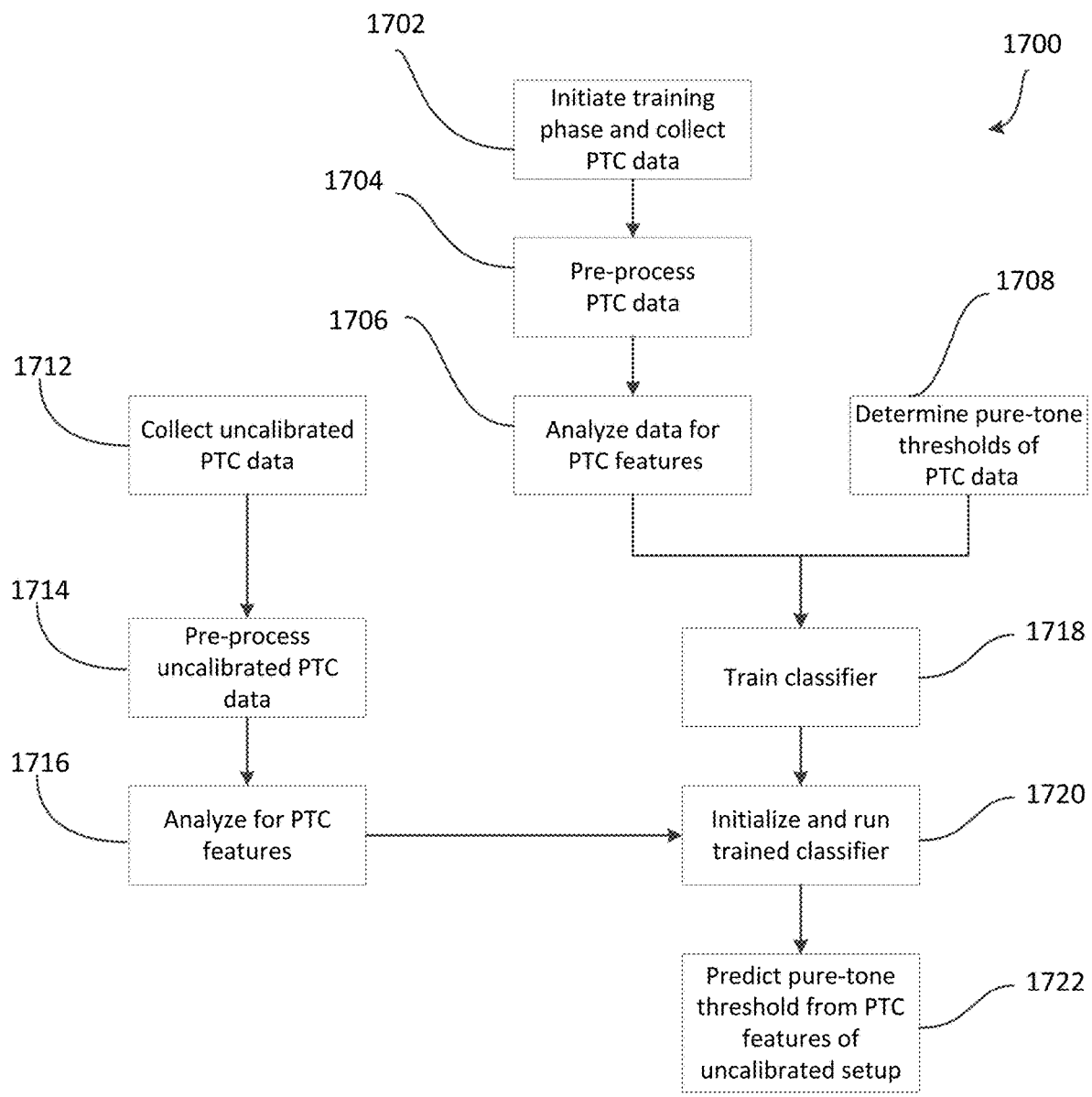
FIG. 17 shows a flow diagram of a method to predict pure-tone thresholds.

FIG. 17 illustrates a flow diagram of a method 1700 of the present disclosure for predicting pure-tone thresholds based on PTC features of an uncalibrated setup. At 1702, a training phase is initiated, wherein a calibrated setup is performed and PTC data are collected. At 1704, the collected PTC data is pre-processed and then analyzed for PTC features at 1706. At 1718, a classifier is trained, taking as input the PTC features from 1706 (also referred to as characterizing parameters) as well as related pure-tone thresholds of PTC data that are determined at 1708. A prediction phase starts at 1712, in which PTC data are collected on an uncalibrated setup. These uncalibrated PTC data are pre-processed at 1714 and then analyzed for PTC features at 1714. At 1720, the classifier is initialized and run using the setup that was developed during the training phase of 1718. The initialized trained classifier then predicts, at 1722, at least one pure-tone threshold based on the PTC features of the uncalibrated setup from 1712.

Figure 18:
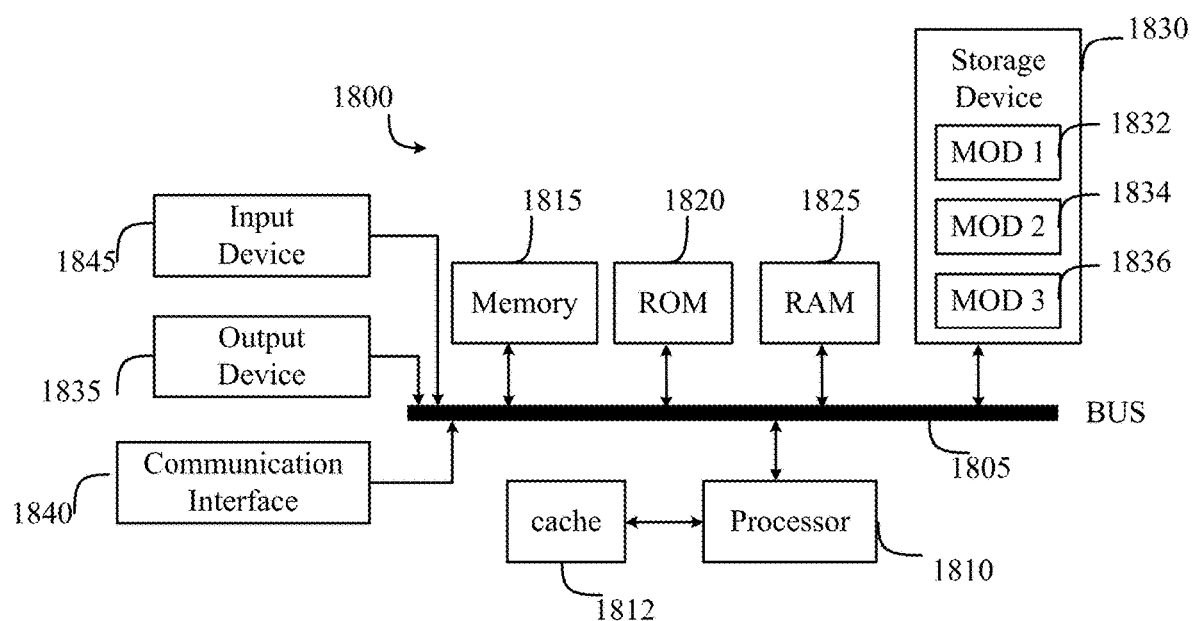
FIG. 18 depicts an example of a system for implementing certain aspects of the present disclosure.

FIG. 18 shows an example of computing system 1800 (e.g., audio device, smart phone, etc.) in which the components of the system are in communication with each other using connection or bus 1805. Connection 1805 can be a physical connection via a bus, or a direct connection into processor 1810, such as in a chipset architecture. Connection 1405 can also be a virtual connection, networked connection, or logical connection.

In some embodiments computing system 1800 is a distributed system in which the functions described in this disclosure can be distributed within a datacenter, multiple datacenters, a peer network, etc. In some embodiments, one or more of the described system components represents many such components each performing some or all of the function for which the component is described. In some embodiments, the components can be physical or virtual devices.

Example system 1800 includes at least one processing unit (CPU or processor) 1810 and connection 1805 that couples various system components including system memory 1815, such as read only memory (ROM) 1820 and random access memory (RAM) 1825 to processor 1810. Computing system 1800 can include a cache of high-speed memory connected directly with, in close proximity to, or integrated as part of processor 1810.

Processor 1810 can include any general-purpose processor and a hardware service or software service, such as services 1832, 1834, and 1836 stored in storage device 1830, configured to control processor 1810 as well as a special-purpose processor where software instructions are incorporated into the actual processor design. Processor 1810 may essentially be a completely self-contained computing system, containing multiple cores or processors, a bus, memory controller, cache, etc. A multi-core processor may be symmetric or asymmetric.

To enable user interaction, computing system 1800 includes an input device 1845, which can represent any number of input mechanisms, such as a microphone for speech, a touch-sensitive screen for gesture or graphical input, keyboard, mouse, motion input, speech, etc. In some examples, the input device can also include audio signals, such as through an audio jack or the like. Computing system 1800 can also include output device 1835, which can be one or more of a number of output mechanisms known to those of skill in the art. In some instances, multimodal systems can enable a user to provide multiple types of input/output to communicate with computing system 1800. Computing system 1800 can include communications interface 1840, which can generally govern and manage the user input and system output. In some examples, communication interface 1840 can be configured to receive one or more audio signals via one or more networks (e.g., Bluetooth, Internet, etc.). There is no restriction on operating on any particular hardware arrangement and therefore the basic features here may easily be substituted for improved hardware or firmware arrangements as they are developed.

Storage device 1830 can be a non-volatile memory device and can be a hard disk or other types of computer readable media which can store data that are accessible by a computer, such as magnetic cassettes, flash memory cards, solid state memory devices, digital versatile disks, cartridges, random access memories (RAMs), read only memory (ROM), and/or some combination of these devices.

The storage device 1830 can include software services, servers, services, etc., that when the code that defines such software is executed by the processor 1810, it causes the system to perform a function. In some embodiments, a hardware service that performs a particular function can include the software component stored in a computer-readable medium in connection with the necessary hardware components, such as processor 1810, connection 1805, output device 1835, etc., to carry out the function.

The presented technology offers a novel way of evaluating hearing health as well as an effective means of comparing the perceptual rescue offered by digital signal processing algorithms. It is to be understood that the present invention contemplates numerous variations, options, and alternatives. The present invention is not to be limited to the specific embodiments and examples set forth herein.

It should be further noted that the description and drawings merely illustrate the principles of the proposed device. Those skilled in the art will be able to implement various arrangements that, although not explicitly described or shown herein, embody the principles of the invention and are included within its spirit and scope. Furthermore, all examples and embodiment outlined in the present document are principally intended expressly to be only for explanatory purposes to help the reader in understanding the principles of the proposed device. Furthermore, all statements herein providing principles, aspects, and embodiments of the invention, as well as specific examples thereof, are intended to encompass equivalents thereof.

What is claimed is:

1. A method comprising:
    transforming an input audio sample into the frequency domain;
    applying a first hearing profile to the input audio sample to generate a first perceptually relevant information (PRI) value for the input audio sample, wherein perceptually relevant information is calculated by calculating perceptual entropy;
    applying a second hearing profile to the input audio sample to generate a second perceptually relevant information value for the input audio sample, wherein perceptually relevant information is calculated by calculating perceptual entropy; and
    analyzing the first and second PRI values to generate a PRI index value for a given user.

2. The method of claim 1, further comprising:
    processing the input audio sample using a parameterized processing function to generate a processed audio sample;

applying the second hearing profile to the processed audio sample to calculate a third perceptually relevant information value for the processed audio sample; and analyzing the first, second, and third PRI values to determine a perceptual rescue effected by the parameterized processing function.

3. The method of claim 2, wherein:

the perceptual rescue effected by the parameterized processing function is optimized by determining at least one processing parameter by a sequential determination of subsets of the at least one processing parameter, each subset determined so as to optimize the given user's perceptually relevant information for the input audio signal.

4. The method of claim 3, wherein:

the parameterized processing function operates on one or more subband signals of the input audio signal; and the perceptual rescue effected by the parameterized processing function is optimized by:

selecting a subset of the subbands so that a masking interaction between the selected subset of subbands is minimized;

determining at least one first processing parameter for the selected subbands; and determining at least one second processing parameter for an unselected subband based on the first processing parameters of adjacent subbands.

5. The method of claim 4, wherein the at least one second processing parameter for an unselected subband is determined based on an interpolation of the first processing parameters of adjacent subbands.

6. The method of claim 4, wherein the at least one first processing parameter is determined sequentially on a subband by subband basis.

7. The method of claim 3, wherein the parameterized processing function operates on one or more subband signals of the input audio signal, the method further comprising:

selecting a subset of adjacent subbands;

tying the corresponding values of the at least one processing parameter for each subband of the selected subset of adjacent subbands; and performing a joint determination of the tied processing parameter values by minimizing the given user's perceptually relevant information for the selected subset of adjacent subbands.

8. The method of claim 7, further comprising:

selecting a reduced subset of adjacent subbands from the selected subset of adjacent subbands;

tying the corresponding values of the at least one processing parameter for each selected subband of the reduced subset of subbands;

performing a joint determination of the tied parameter values by minimizing the given user's perceptually relevant information for the reduced subset of subbands;

repeating the previous steps until a first single subband is selected as the reduced subset of adjacent subbands; and determining a first processing parameter of the first single subband.

9. The method of claim 8, further comprising:

selecting a second subset of adjacent subbands;

successively reducing the selected second subset of adjacent subbands until a second single subband is selected;

determining a second processing parameter of the second single subband; and performing a joint processing of the first processing parameter of the first single subband and the second processing parameter of the second single subband.

10. The method of claim 9, wherein the joint processing of the first and second processing parameter comprises at least one of:

joint optimization of the processing parameters for the derived single subbands;

smoothing of the parameters for the derived single subbands; and applying constraints on the deviation of corresponding values of the processing parameters for the derived single subbands.

11. The method of claim 1, further comprising measuring the perceptual rescue of a plurality of parameterized processing functions by:

separately processing the input audio sample using the plurality of parameterized processing functions to generate a plurality of processed audio samples;

applying the second hearing profile to each processed audio sample to calculate a perceptually relevant information value for each parameterized processing function, wherein the second hearing profile is obtained from the given user and comprises masking threshold and hearing threshold information; and for each parameterized processing function, analyzing the calculated perceptually relevant information value to generate a corresponding PRI index value uniquely associated with the given user and the parameterized processing function.

12. The method of claim 1, wherein:

the first hearing profile is obtained from a healthy human listener and the second hearing profile is obtained from the given user; and the first hearing profile and the second hearing profile comprise one or more of masking threshold information and hearing threshold information.

13. The method of claim 12, further comprising:

determining one or more portions of the masking threshold information from masking threshold curves, the masking threshold curves corresponding to the first hearing profile and the second hearing profile; and determining one or more portions of the hearing threshold information from audiogram data.

14. The method of claim 12, wherein:

the first PRI value represents a healthy standard PRI value;

the second PRI value represents the given user's unique PRI value; and generating the PRI index value for the given user comprises calculating a ratio value based on the first PRI value and the second PRI value.

15. The method of claim 1, wherein one or more of the first hearing profile and the second hearing profile are derived from at least one of a suprathreshold test, a psychophysical tuning curve, a masked threshold test, a threshold test and an audiogram.

16. The method of claim 1, in which the second hearing profile is the given user's hearing profile and is estimated from demographic information of the given user.

17. An audio processing device comprising:

at least one processor; and at least one memory storing instructions, which when executed causes the at least one processor to:

transform an input audio sample into the frequency domain;

apply a first hearing profile to the input audio sample to generate a first perceptually relevant information (PRI) value for the input audio sample, wherein perpetually relevant information is calculated by calculating perceptual entropy;

apply a second hearing profile to the input audio sample to generate a second perceptually relevant information value for the input audio sample, wherein perceptually relevant information is calculated by calculating perceptual entropy; and analyze the first and second PRI values to generate a PRI index value for a given user.

18. The audio processing device of claim 17, wherein the instructions further cause the at least one processor to:

process the input audio sample using a parameterized processing function to generate a processed audio sample;

apply the second hearing profile to the processed audio sample to generate a third perceptually relevant information value for the processed audio sample; and analyze the first, second, and third PRI values to determine a perceptual rescue effected by the parameterized processing function.

19. The audio processing device of claim 17, wherein the instructions further cause the at least one processor to measure the perceptual rescue of a plurality of parameterized processing functions by:

separately processing the input audio sample using the plurality of parameterized processing functions to generate a plurality of processed audio samples;

applying the second hearing profile to each processed audio sample to calculate a perceptually relevant information value for each parameterized processing function, wherein the second hearing profile is obtained from the given user and comprises masking threshold and hearing threshold information; and for each parameterized processing function, analyzing the calculated perceptually relevant information value to generate a corresponding PRI index value uniquely associated with the given user and the parameterized processing function.

* * * * *